United States Patent [19]
Fenkl et al.

[11] Patent Number: 5,626,791
[45] Date of Patent: May 6, 1997

[54] AROMATIC COMPOUNDS, AND THEIR USE IN LIQUID-CRYSTALLINE MIXTURES

[75] Inventors: Franz Fenkl, Kelsterbach; Javier Manero, Frankfurt; Hubert Schlosser, Glashütten; Dietmar Jungbauer, Weiterstadt, all of Germany

[73] Assignee: Hoechst Aktiengesellschaft, Frankfurt, Germany

[21] Appl. No.: 284,796

[22] Filed: Aug. 2, 1994

[30] Foreign Application Priority Data

Aug. 4, 1993 [DE] Germany .............. 43 26 151.5

[51] Int. Cl.$^6$ .............. C09K 19/52; C09K 19/34
[52] U.S. Cl. .............. 252/299.01; 252/299.61
[58] Field of Search .............. 252/299.01, 299.61

[56] References Cited

FOREIGN PATENT DOCUMENTS

| | | |
|---|---|---|
| 0546338 | 6/1993 | European Pat. Off. . |
| 0555843 | 8/1993 | European Pat. Off. . |
| 0571955 | 12/1993 | European Pat. Off. . |
| 0611815 | 8/1994 | European Pat. Off. . |
| 3908269 | 9/1990 | Germany . |
| 4218978 | 12/1993 | Germany . |
| 62-195355 | 8/1962 | Japan . |

OTHER PUBLICATIONS

CA:51: 3906f, 1957.
CA67: 20661, 1967.
German Abstract No. 3908269–A published Mar. 14, 1989.
Chemical Abstract, vol. 100, No. 15, Apr. 9, 1984, Abstract No. 121044. "4-(Trans-4-n-Alkylcyclohexyl)phenyl piperonylates".

Derwent Abstrct No. J60069055 published Apr. 19, 1985.

German Abstract No. DE 4218978 published Jun. 10, 1992.

*Primary Examiner*—Cynthia Harris Kelly
*Attorney, Agent, or Firm*—Curtis, Morris & Safford, PC.

[57] ABSTRACT

An aromatic compound of the formula (I)

$$R^1(-A^1)_a(-M^1)_b(-A^2)_c(-M^2)_d-B(-M^3)_e(-A^3)_f(-M^4)_g(-A^4)_h-R_2 \quad (I)$$

in which

B is one of the two following aromatic groups:

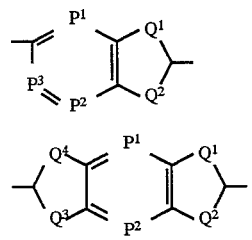

$Q^1$, $Q^2$, $Q^3$ and $Q^4$ are identical or different and are $CH_2$, $CF_2$, $N-R^3$, S, O or $C=O$;

$P^1$, $P^2$ and $P^3$ are identical or different and are $C-H$, $C-F$ or N; and the remaining symbols and indicies define mesogenic radicals. The compounds are suitable as components of liquid-crystalline mixtures.

7 Claims, No Drawings

AROMATIC COMPOUNDS, AND THEIR USE IN LIQUID-CRYSTALLINE MIXTURES

BACKGROUND OF THE INVENTION

In addition to nematic and cholesteric liquid crystals, optically active tilted smectic (ferroelectric) liquid crystals have also been used recently in commercial display devices.

Clark and Lagerwall have been able to show that the use of ferroelectric liquid crystals (FLCs) in very thin cells results in optoelectrical switching or display elements which have response times faster by a factor of 1000 compared with conventional TN ("twisted nematic") cells (cf., for example, EP-A 0 032 362). On the basis of this and other favorable properties, for example the possibility of bistable switching and the virtually viewing angle-independent contrast, FLCs are fundamentally highly suitable for areas of application such as computer displays.

For the use of FLCs in electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_C$ phase can be achieved, for example, if the phase sequence of the liquid-crystal mixture is, with decreasing temperature:

isotropic→N*→$S_A$→$S^*_C$

The prerequisite is that the pitch of the helix in the N* phase is very large (greater than 10 µm) or even better is fully compensated (see, for example, T. Matsumoto et al., pp. 468–470, Proc. of the 6th Int. Display Research Conf., Japan Display, Sep. 30 –Oct. 2, 1986, Tokyo, Japan; M. Murakami et al., ibid. pp. 344–347). This is achieved by adding one or more optically active dopes which induce a right-hand helix to the chiral liquid-crystal mixture which has, for example, a left-hand helix in the N* phase, in such amounts that the helix is compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213–134 and 114 (1984), 151–187). As in the case of the cholesteric pitch, this is achieved by using dopes having the opposite rotation of the helix.

The optical response time γ [µs] of ferroelectric liquid-crystal systems, which should be as short as possible, depends on the rotational viscosity of the system y[mPas], the spontaneous polarization $P_s$[nC/cm$^2$] and the electric field strength E[V/m], in accordance with the equation $$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably ≈0.13, and a low positive or preferably negative dielectric anisotropy Δε are required (see, for example, S. T. Lagerwall et al., "Ferroelectric Liquid Crystals for Displays", SID Symposium, Oct. Meeting 1985, San Diego, Calif., USA).

The totality of these requirements can only be achieved by means of mixtures comprising a plurality of components. The base (or matrix) used preferably comprises compounds which if possible themselves already have the desired phase sequence I→N→$S_A$→$S_C$. Further components of the mixture are frequently added in order to reduce the melting point and to broaden the $S_C$ and usually also the N phase, to induce optical activity, for pitch compensation and to match the optical and dielectric anisotropy; further, the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP-A 0 405 346. In contrast to the SSFLCD effect, utilization of these effects requires a liquid-crystalline material having a short $S_C$ pitch.

Since the development of ferroelectric liquid-crystal mixtures in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

The object of the present invention was therefore to provide novel compounds which are suitable in liquid-crystalline mixtures for improving the property profile of these mixtures.

JP-A-62/195,355 and EP-A-0 546 338 describe indane derivatives and their use in liquid-crystal mixtures.

SUMMARY OF THE INVENTION

It has now been found, surprisingly, that fused carbocyclic and heterocyclic ring systems comprising an aromatic six-membered ring and one or two aliphatic five-membered rings are particularly suitable for use in liquid-crystal mixtures.

The invention therefore relates to compounds of the formula (I)

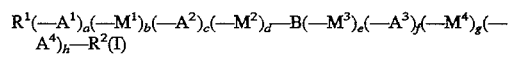

in which the symbols and indices have the following meanings:

B is one of the two following aromatic groups:

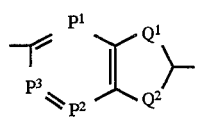

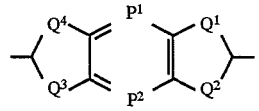

$R^1$ and $R^2$ are identical or different and are hydrogen, —CN, —F, —Cl, —CF$_3$, —CHF$_2$, —CH$_2$F, —OCF$_3$, —OCHF$_2$, —OCH$_2$F or a straight-chain or branched alkyl radical having 1 to 20 carbon atoms (with or without an asymmetrical carbon atom), where one or more —CH$_2$— groups may also be replaced by —O—, —S—, —CO—, —CS—, —CH=CH—, —C≡C—, —Si(CH$_3$)$_2$—, 1,4-phenylene, trans-1,4-cyclohexylene or trans-1,3-cyclopentylene, with the proviso that oxygen atoms and sulfur atoms must not be bonded directly to one another, and/or one or more H atoms of the alkyl radical may be substituted by —F, —Cl, —Br, —OR$^2$, —SCN, —OCN or —N$_3$, or are alternatively one of the following chiral groups:

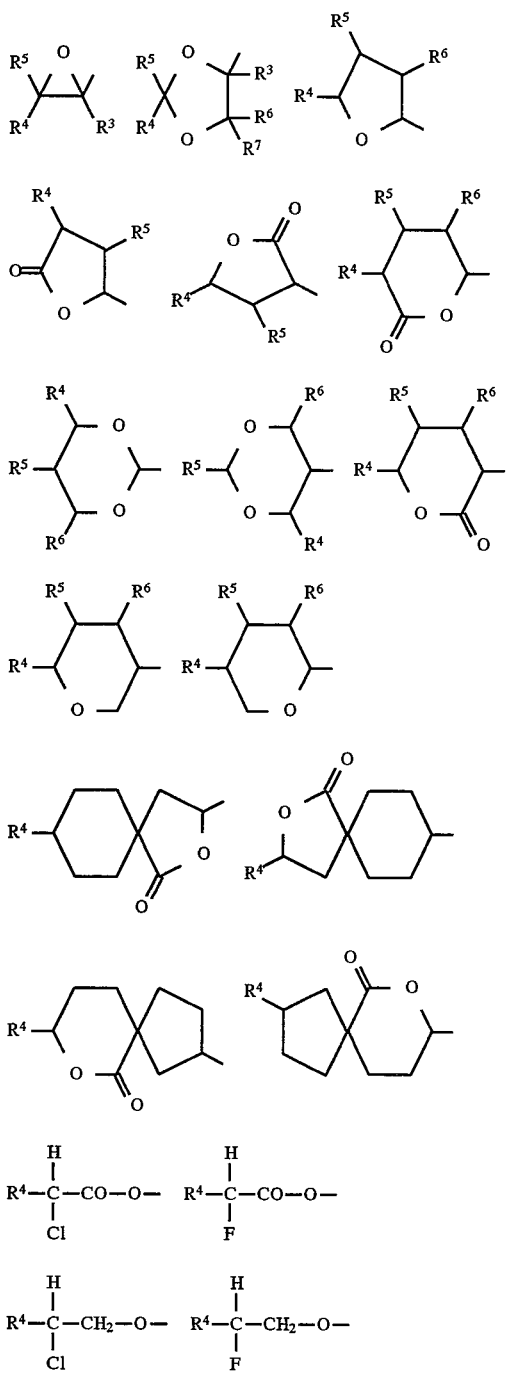

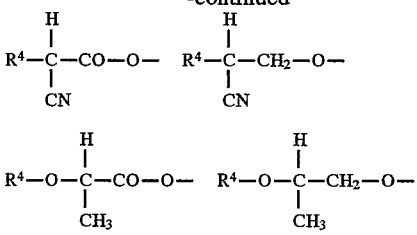

R$^3$, R$^4$, R$^5$, R$^6$ and R$^7$ are identical or different and are hydrogen or a straight-chain or branched alkyl radical having 1–16 carbon atoms (with or without an asymmetrical carbon atom), where one or more —CH$_2$— groups may also be replaced by —O— or —CH=CH—, with the proviso that oxygen atoms must not be bonded directly to one another, and/or one or more H atoms of the alkyl radical may be substituted by —F or —Cl; R$^4$ and R$^5$ may also together be —(CH$_2$)$_4$— or —(CH$_2$)$_5$— if they are bonded to an oxirane, dioxolane, tetrahydrofuran, tetrahydropyran, butyrolactone or valerolactone system;

Q$^1$, Q$^2$, Q$^3$ and Q$^4$ are identical or different and are CH$_2$, CF$_2$, N—R$^3$, S, O or C=O;

P$^1$, P$^2$ and P$^3$ are identical or different and are C—H, C—F or N;

M$^1$, M$^2$, M$^3$ and M$^4$ are identical or different and are —O—, —S—, —CO—, —CO—O—, —O—CO—, —O—CO—O—, —CO—S—, —S—CO—, —CS—O—, —O—CS—, —S—CS—S—, —O—CS—O—, —S—CO—S—, —CS—, —CH$_2$—O—, —O—CH$_2$—, —CH$_2$—S—, —S—CH$_2$—, —CH=CH—, —C—C—, —O—CO—C≡C—, —C≡C—COO—, —O—CO—CH=CH—, —CH=CH—COO—, —O—CO—CH$_2$—CH$_2$—, —CH$_2$—CH$_2$—COO—, —O—CH$_2$—C≡C—, —C≡C—CH$_2$—O—, —O—CH$_2$—CH=CH—, —CH=CH—CH$_2$—O—, —O—CH$_2$—CH$_2$—CH$_2$—, —CH$_2$—CH$_2$—CH$_2$—O— or a single bond;

A$^1$, A$^2$, A$^3$ and A$^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH$_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4odiyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]octane-1,4-diyl, in which one or more H atoms may be replaced by F, Cl and/or CN, 1,3-dioxaborinane-2,5-diyl or the group B;

a, b, c, d, e, f, g and h are zero or one;
with the following proviso:

If the group B is

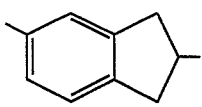

at least one of the radicals R¹ must contain an —Si(CH3)₂— and/or ∧ group and/or be one of the following chiral groups:

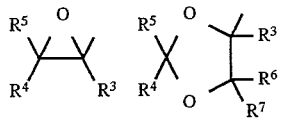

The compounds according to the invention are highly suitable, in particular, for the induction or broadening of nematic phases in liquid-crystal mixtures, in particular ferroelectric mixtures, and for the preparation of ferroelectric liquid-crystal mixtures with a high spontaneous polarization value $P_S$.

DESCRIPTION OF THE PREFERRED EMBODIMENTS

Preference is given to compounds of the formula I in which the symbols and indices have the following meanings:

$R^1$ and $R^2$ are identical or different and are hydrogen, —CN, —F, —Cl, —CF₃, —CHF₂, —CH₂F, —OCF₃, —OCHF₂, —OCH₂F or a straight-chain or branched alkyl radical having 1 to 18 carbon atoms (with or without an asymmetrical carbon atom), where one or more —CH₂— groups may also be replaced by —O—, —CO—, —CH=CH—, —C≡C—, ∧, —Si(CH₃)₂— or trans-1, 4-cyclohexylene, with the proviso that oxygen atoms must not be bonded directly to one another, and/or one or more H atoms of the alkyl radical may be substituted by —F, —Cl, —OR³, —OCN or —N₃, or are alternatively one of the following chiral groups:

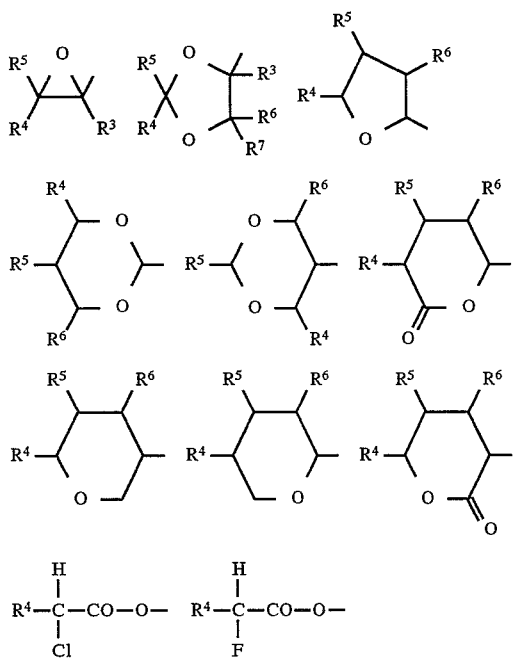

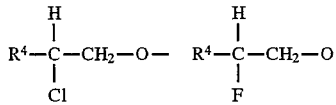

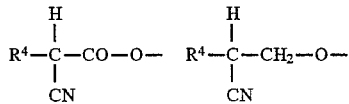

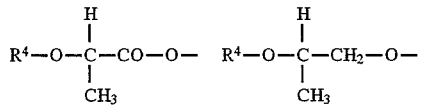

$R^3$, $R^4$, $R^5$, $R^6$ and $R^7$ are identical or different and are hydrogen or a straight-chain or branched alkyl radical having 1–16 carbon atoms (with or without an asymmetrical carbon atom), where one or more —CH₂— groups may also be replaced by —O— or —CH=CH—, with the proviso that oxygen atoms must not be bonded directly to one another, and/or one or more H atoms of the alkyl radical may be substituted by —F or —Cl; $R^4$ and $R^5$ may also together be —(CH₂)₄— or —(CH₂)₅— if they are bonded to an oxirane, dioxolane, tetrahydrofuran, tetrahydropyran, butyrolactone or valerolactone system;

$Q^1$, $Q^2$, $Q^3$ and $Q^4$ are identical or different and are CH₂, CF₂, N—R³, O or C=O;

$P^1$, $P^2$ and $P^3$ are identical or different and are C—H, C—F or N;

$M^1$, $M^2$, $M^3$ and $M^4$ are identical or different and are —O—, —CO—, —CO—O—, —O—CO—, —O—CO—O—, —O—CS—O—, —CH₂—O—, —O—CH₂—, —CH=CH—, —C≡C—, —O—CO—C≡C—, —C≡C—COO—, —O—CO—CH=CH—, —CH=CH—COO—, —O—CO—CH₂—CH₂—, —CH₂—CH₂—COO—, —O—CH₂—C≡C—, —C≡C—CH₂—O—, —O—CH₂—CH=CH—, —CH=CH—CH₂—O—, —O—CH₂—CH₂—CH₂—, —CH₂—CH₂—CH₂—O— or a single bond;

$A^1$, $A^2$, $A^3$ and $A^4$ are identical or different and are 1,4-phenylene, in which one or more H atoms may be replaced by F, Cl and/or CN, pyrazine-2,E-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH₃, 1,3,4-thiadiazole-2,5-diyl, 1,3-dioxane-2,5-diyl, thiophene-2,4-diyl, in which one H atom may be replaced by F, Cl and/or CN, thiophene-2,5-diyl, in which one or two H atoms may be replaced by F, Cl and/or CN, naphthalene-2,6-diyl, in which one or more H atoms may be replaced by F, Cl and/or CN, 1,3-dioxaborinane-2,5-diyl or the group B;

a, b, c, d, e, f, g and h are zero or one;

where the above proviso applies.

Very particular preference is given to compounds of the formula I in which the symbols and indices have the following meanings:

$R^1$ and $R^2$ are identical or different and are hydrogen, —CN, —F, —Cl, or a straight-chain or branched alkyl radical having 1 to 16 carbon atoms (with or without an asymmetrical carbon atom), where one, two or three —CH₂— groups may also be replaced by —O—, —CO—, —CH=CH—, ∧, —Si(CH₃)₂— or trans-1,4- cyclohexylene, with the proviso that oxygen atoms must not be bonded directly to one another, and/or one or more H atoms of the alkyl radical may be substituted by —F, —Cl or —OR³, or are alternatively one of the following chiral groups:

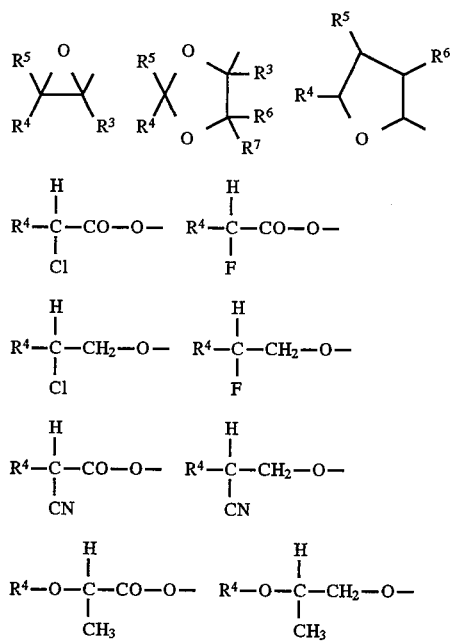

R³, R⁴, R⁵, R⁶ and R⁷ are identical or different and are hydrogen or a straight-chain or branched alkyl radical having 1–14 carbon atoms (with or without an asymmetrical carbon atom), where one or more —CH₂— groups may also be replaced by —O— or —CH=CH—, with the proviso that oxygen atoms must not be bonded directly to one another, and/or one or more H atoms of the alkyl radical may be substituted by —F or —Cl; R⁴ and R⁵ may also together be —(CH₂)₄— or —(CH₂)₅— if they are bonded to an oxirane or dioxolane system;

Q¹, Q², Q³ and Q⁴ are identical or different and are CH₂, CF₂, N—R³, O or C=O;

P¹, P² and P³ are identical or different and are C—H, C—F or N;

M¹, M², M³ and M⁴ are identical or different and are —O—, —CO—, —CO—O—, —O—CO—, —O—CO—O—, —CH₂—O—, —O—CH₂—, —CH=CH—, —O—CO—C≡C—, —C≡C—COO—, —O—CO—CH=CH—, —CH=CH—COO—, —O—CO—CH₂—CH₂—, —CH₂—CH₂—COO—, —O—CH₂—C≡C—, —C≡C—CH₂—O—, —O—CH₂—CH=CH—, —CH=CH—CH₂—O—, —O—CH₂—CH₂—CH₂—, —CH₂—CH₂—CH₂—O— or a single bond;

A¹, A², A³ and A⁴ are identical or different and are 1,4-phenylene, in which one, two or three H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or two H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH₃, 1,3,4-thiadiazole-2,5-diyl, naphthalene-2,6-diyl, in which one or two H atoms may be replaced by F, Cl and/or CN, 1,3-dioxaborinane-2,5-diyl or the group B;

a, b, c, d, e, f, g and h are zero or one;

with the proviso that at least one of the radicals Q¹, Q², Q³ and Q⁴ is —CF₂—, —NR³—, —S—, —O— or —CO— and/or at least one of the radicals P¹, P² and P³ is =CF— or =N—.

Very particular preference is given to compounds of the formula I in which the group B has the following meanings:

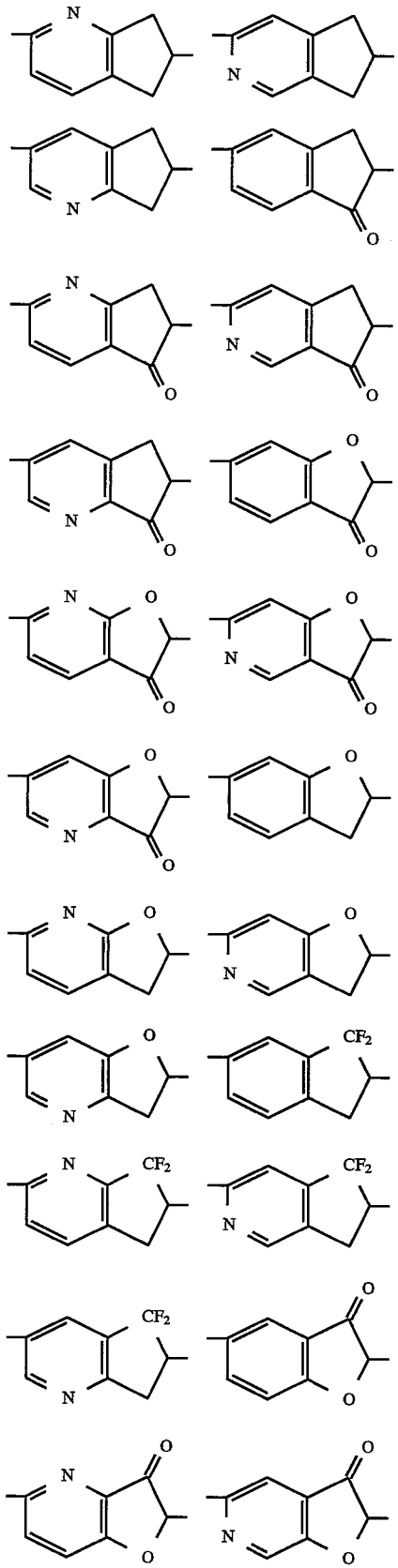

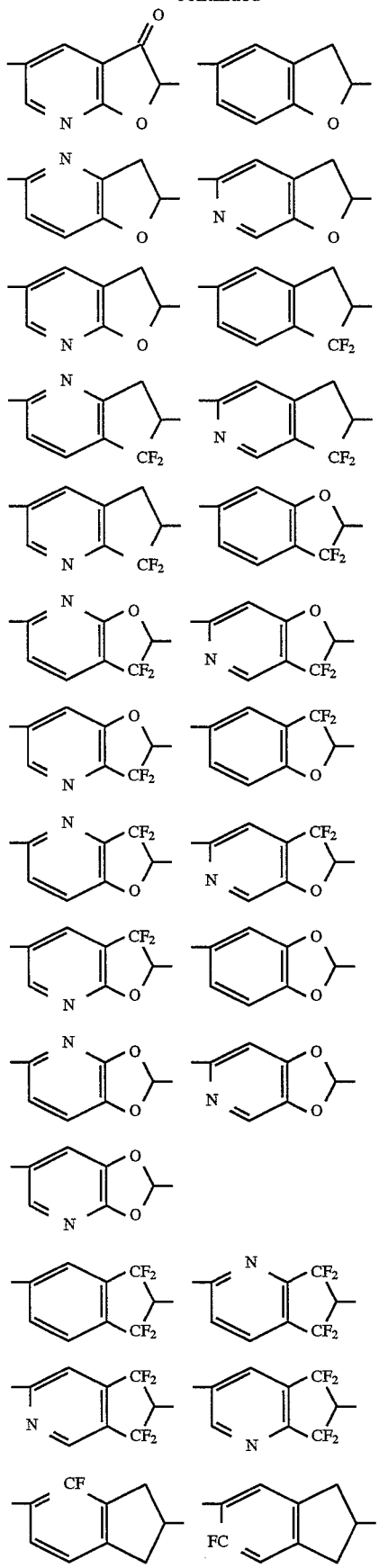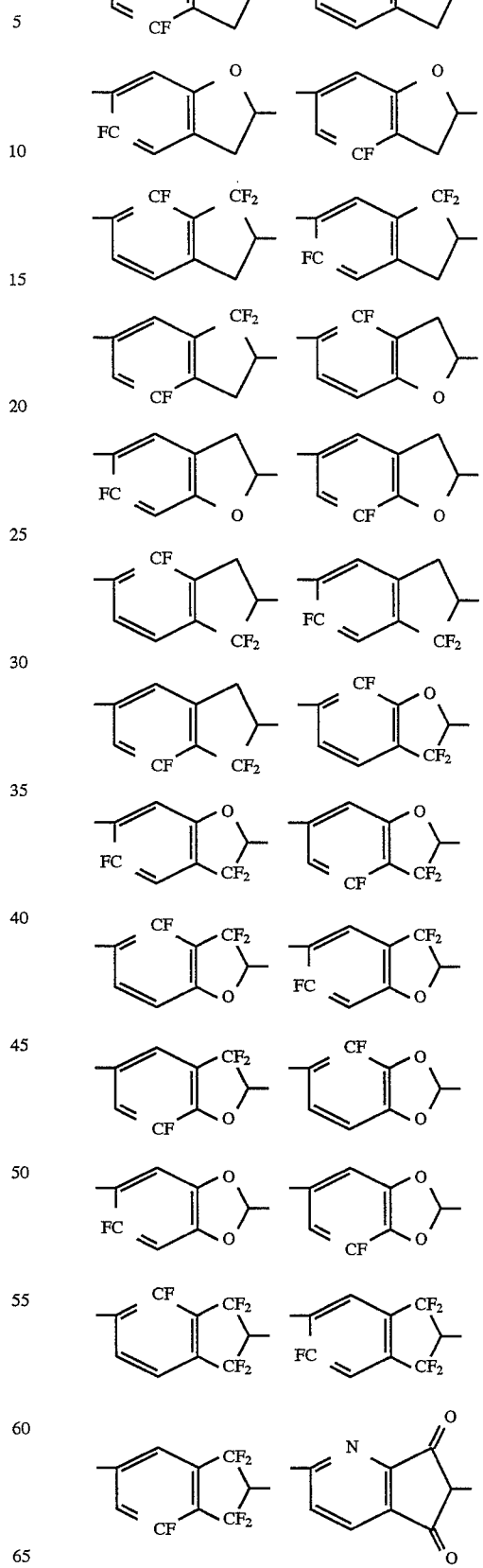

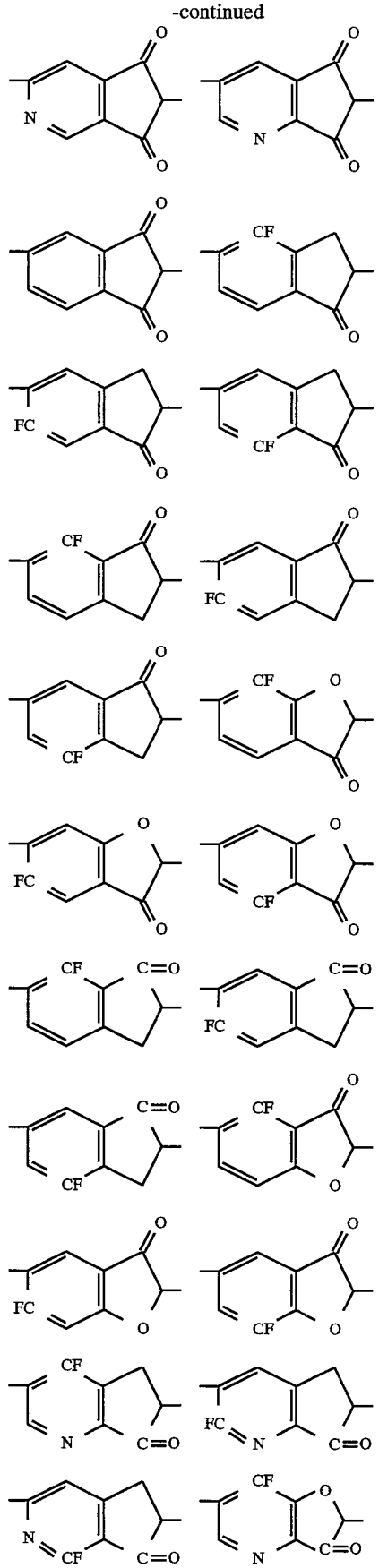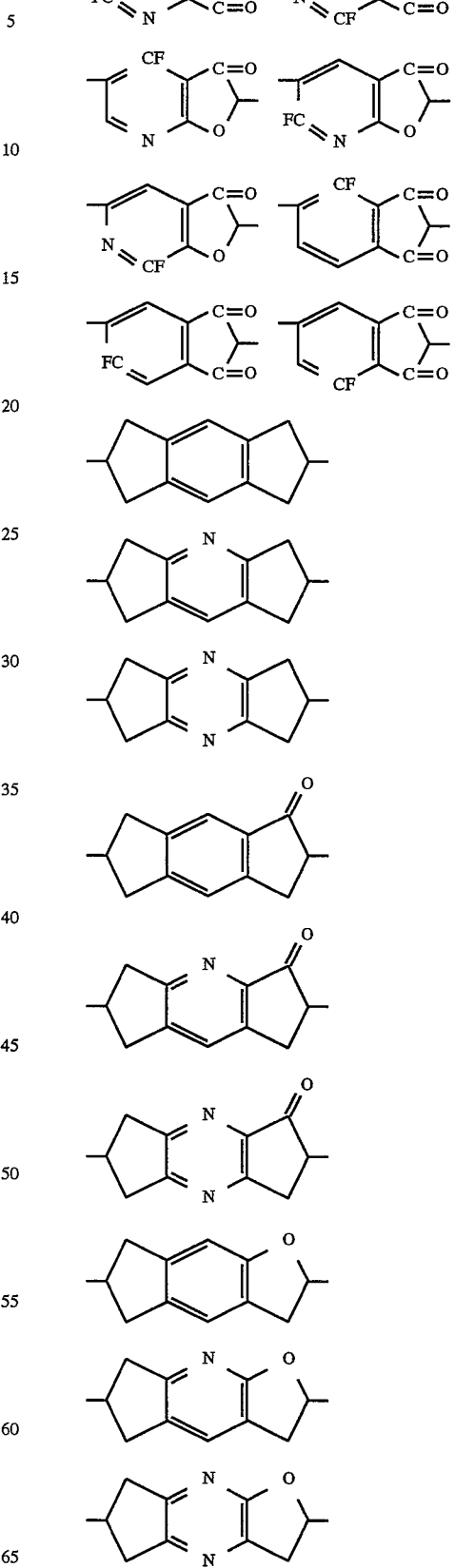

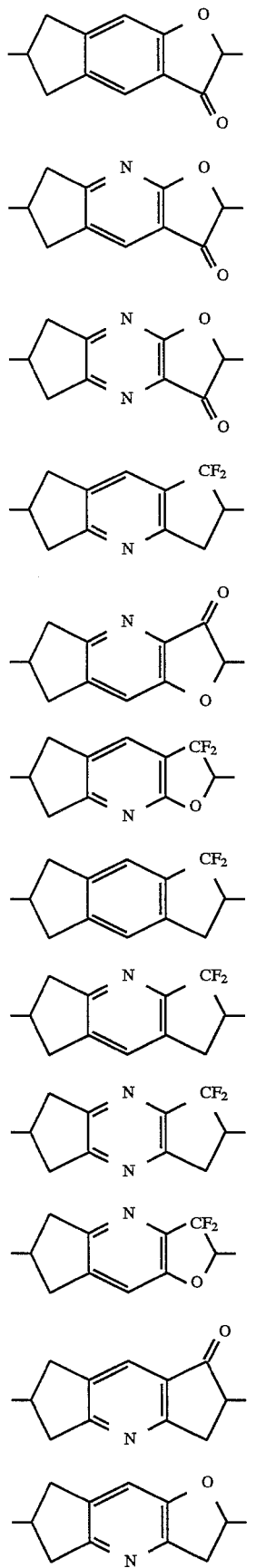
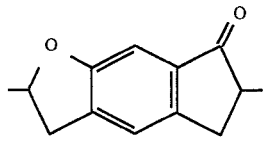
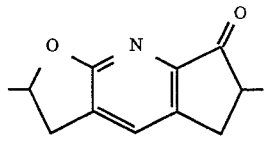
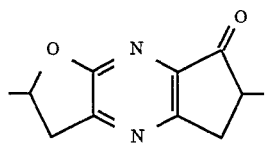
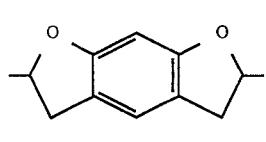
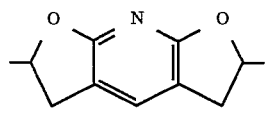
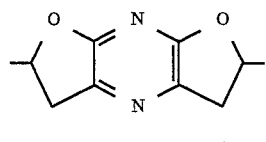
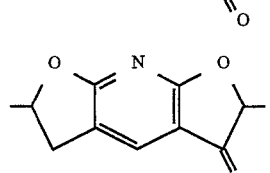
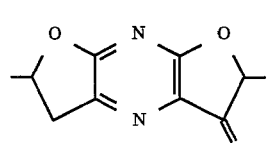
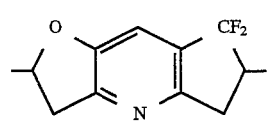
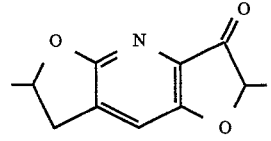
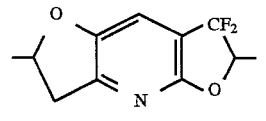

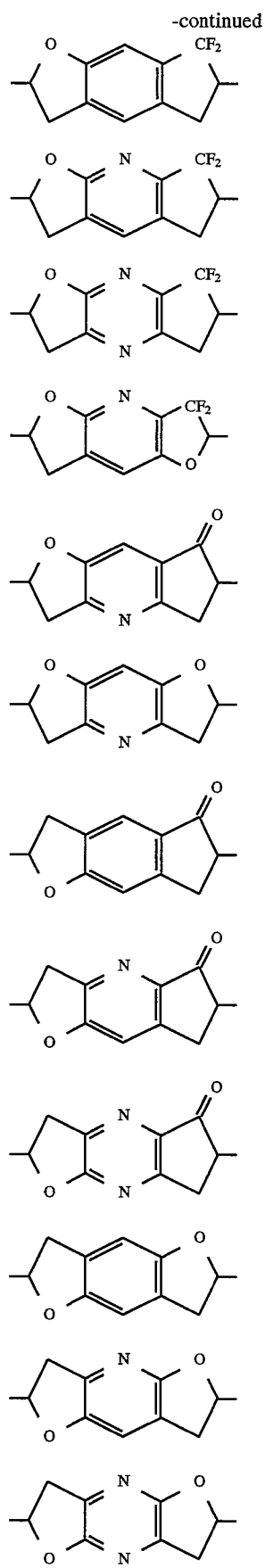
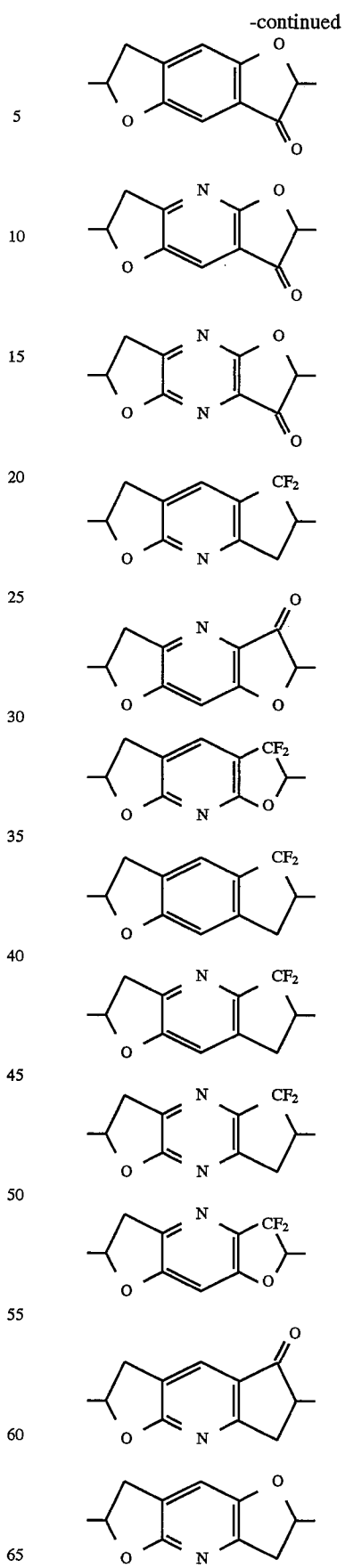

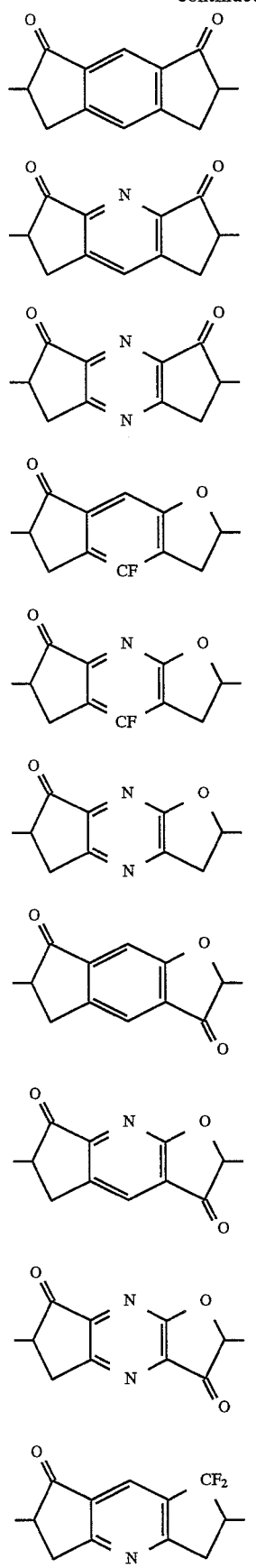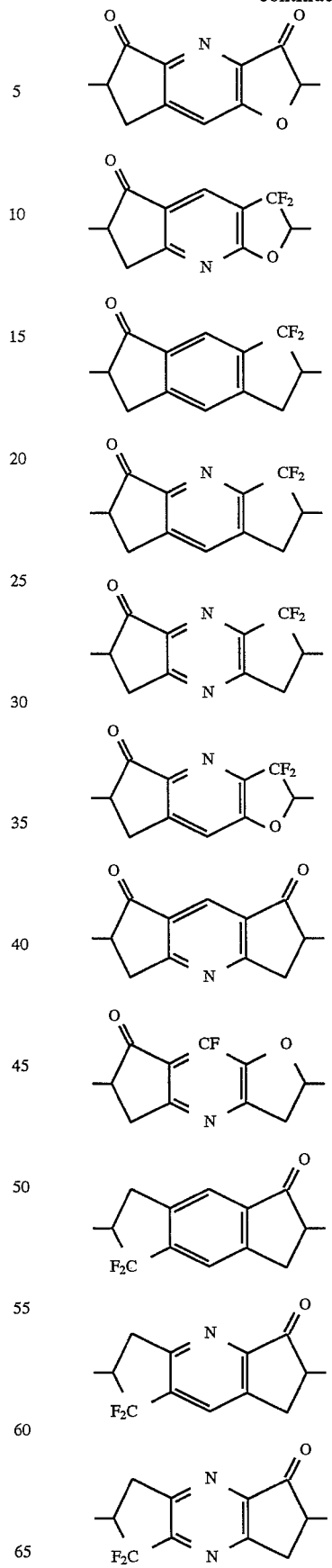

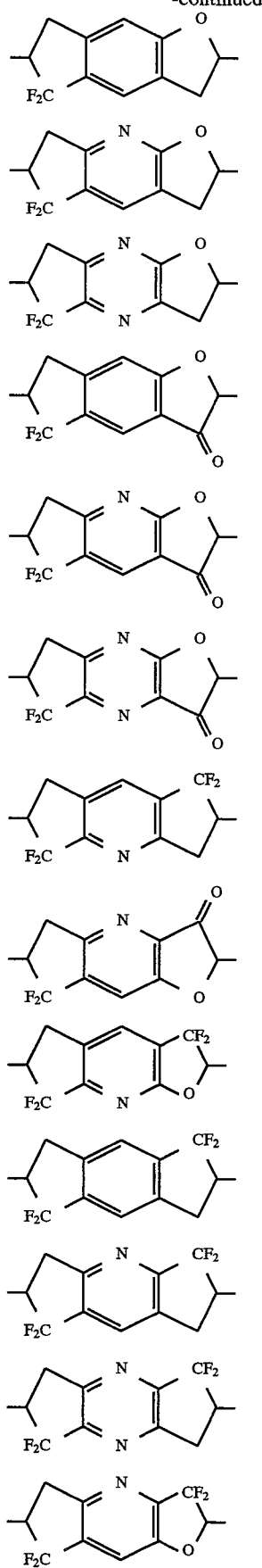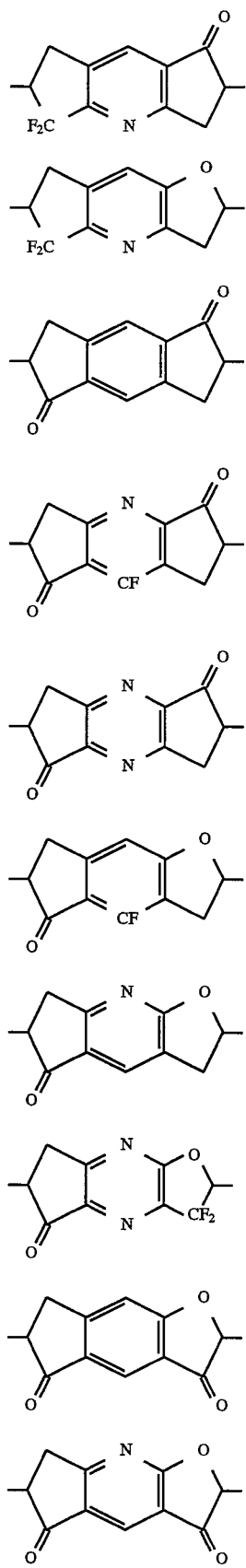

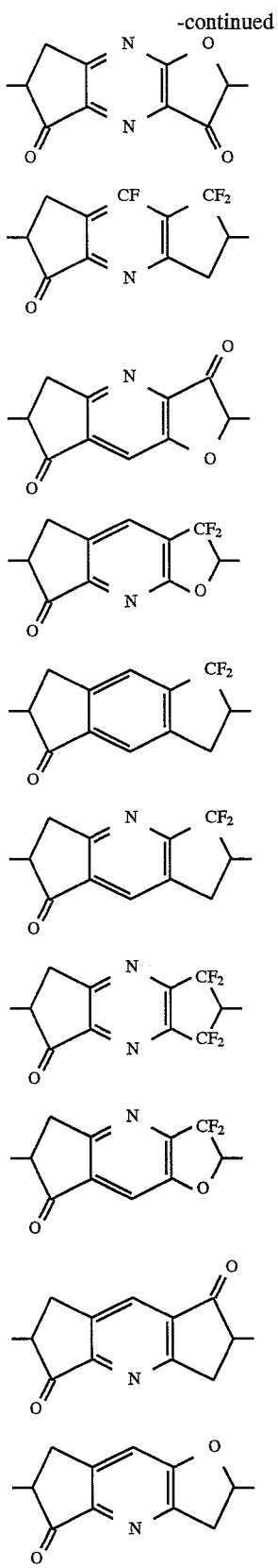

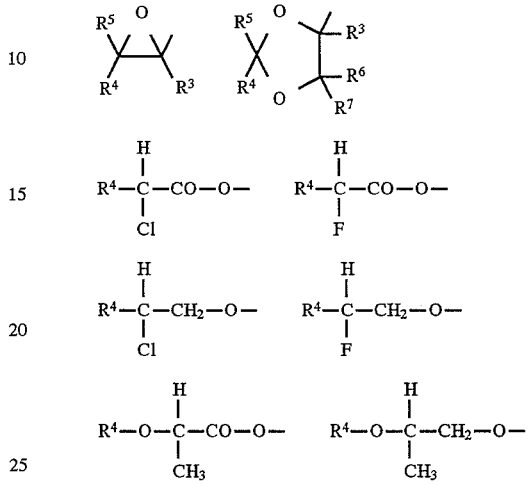

be replaced by —O—, —CO—, —CH=CH—, ∧, —Si(CH₃)₂— or trans-1,4-cyclohexylene, with the proviso that oxygen atoms must not be bonded directly to one another, and/or one or more H atoms of the alkyl radical may be substituted by —F or —OR³ or are alternatively one of the following chiral groups:

$R^3$, $R^4$, $R^5$, $R^6$ and $R^7$ are identical or different and are hydrogen or a straight-chain or branched alkyl radical having 1–10 carbon atoms (with or without an asymmetrical carbon atom), where one or two —CH₂— groups may also be replaced by —O— or —CH=CH—, with the proviso that oxygen atoms must not be bonded directly to one another, and/or one or more H atoms of the alkyl radical may be substituted by —F or —Cl; $R^4$ and $R^5$ may also together be —(CH₂)₄— or —(CH₂)₅— if they are bonded to an oxirane or dioxolane system;

$M^1$, $M^2$, $M^3$ and $M^4$ are identical or different and are —O—, —CO—, —CO—O—, —O—CO—, —O—CO—O—, —CH₂—O—, —O—CH₂—, —O—CO—C≡C—, —C≡C—COO—, —O—CO—CH=CH—, —CH=CH—COO—, —O—CO—CH₂—CH₂—, —CH₂—CH₂—COO—, —O—CH₂—C≡C—, —C≡C—CH₂—O—, —O—CH₂—CH=CH—, —CH=CH—CH₂—O—, —O—CH₂—CH₂—CH₂—, —CH₂—CH₂—CH₂—O— or a single bond;

$A^1$, $A^2$, $A^3$ and $A^4$ are identical or different and are 1,4-phenylene, in which one, two or three H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or two H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH₃, 1,3,4-thiadiazole-2,5-diyl or naphthalene-2,6-diyl, in which one or two H atoms may be replaced by F, Cl and/or CN;

a, b, c, d, e, f, g and h are zero or one.

The compounds according to the invention are prepared by methods known per se from the literature, as described in standard works on organic synthesis, for example Houben-Weyl, Methoden der Organischen Chemie [Methods of Organic Chemistry], Georg-Thieme-Verlag, Stuttgart.

$R^1$ and $R^2$ are identical or different and are hydrogen or a straight-chain or branched alkyl radical having 1 to 16 carbon atoms (with or without an asymmetrical carbon atom), where one, two or three —CH₂— groups may also The preparation is carried out under reaction conditions which are known and suitable for said reactions. Use may also be made here of variants which are known per se, but are not described here in greater detail.

If desired, the starting materials can also be formed in situ, by not isolating them from the reaction mixture, but instead immediately converting them further into the compounds of the formula (I).

A possible synthesis of indane and heteroindane derivatives in which $Q^1$ is $CH_2$ is shown in reaction schemes A and B below:

Scheme A:

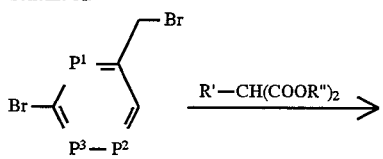

R'—CH(COOR")$_2$

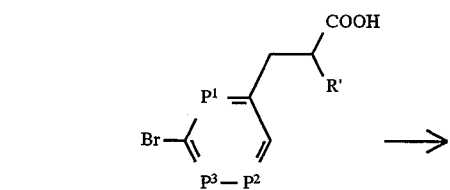

Scheme A:

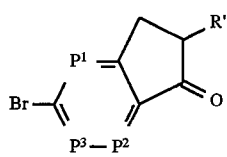

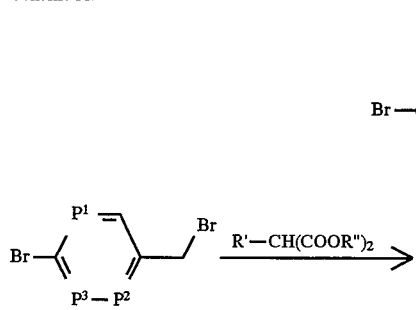

R'—CH(COOR")$_2$

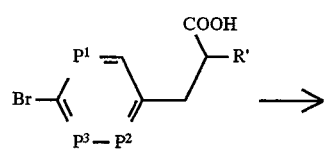

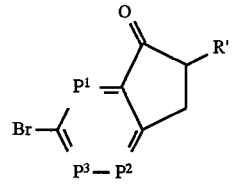

Scheme B:
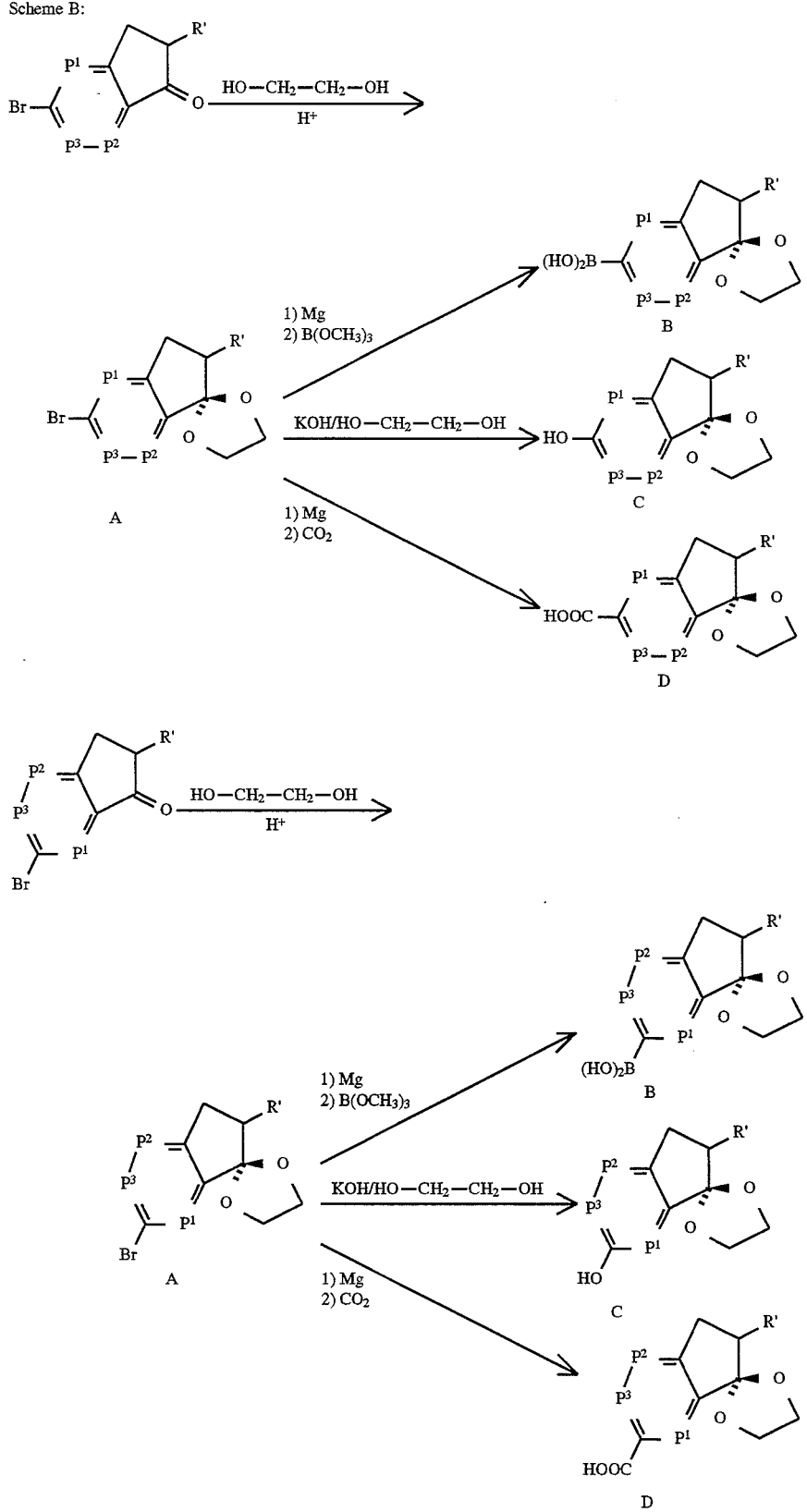
A possible synthesis of dihydrobenzofurans and heterodihydrobenzofuran derivatives in which $Q^1$ is O is shown in reaction schemes C and D below:

Scheme C:
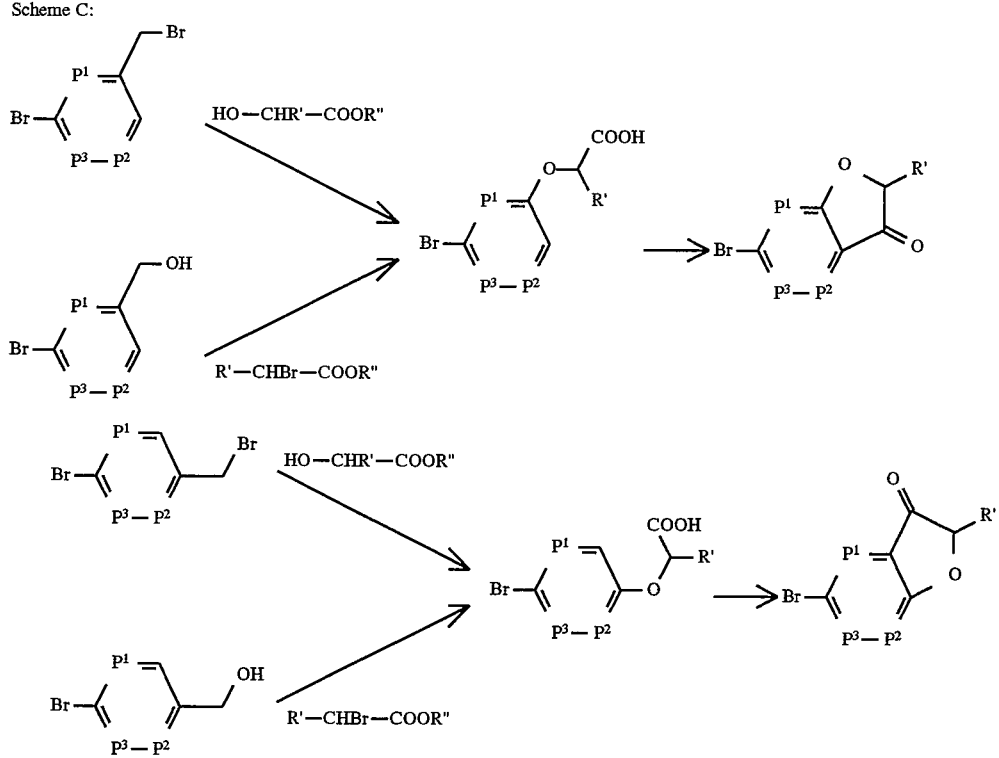
Scheme D:
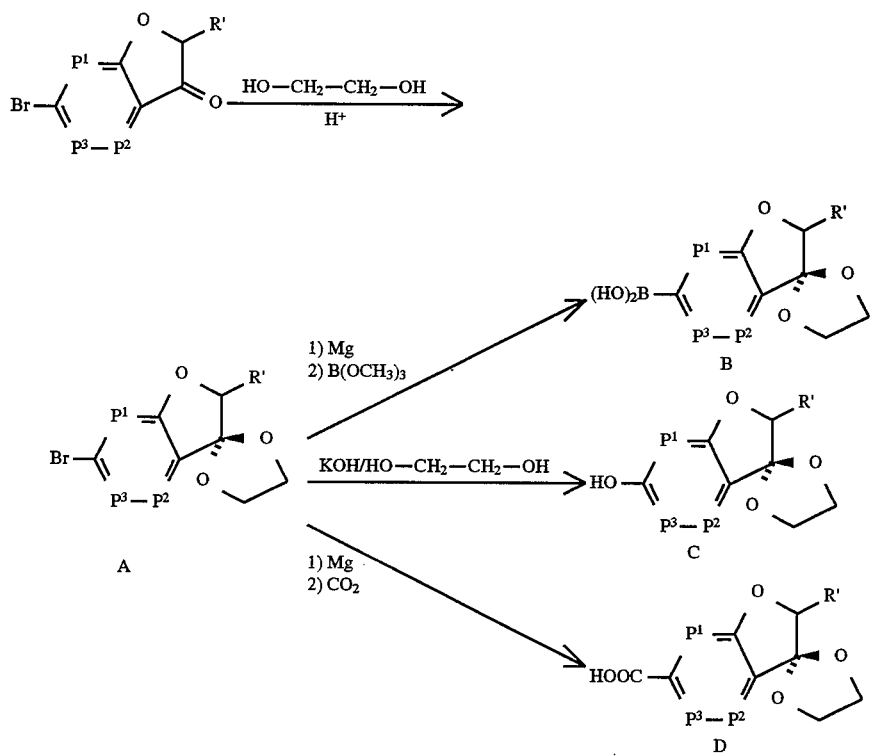

Scheme D:
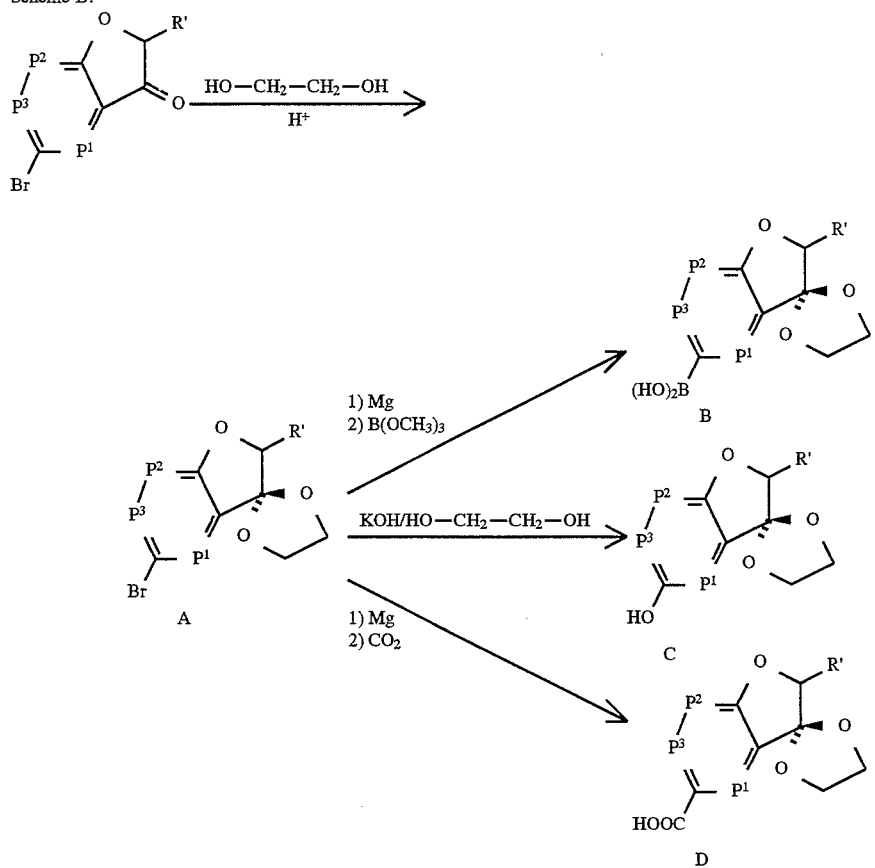
Schemes E and F below show in illustrative terms the synthesis of derivatives in which $Q^1$ and $Q^2$ are O:
Scheme E:
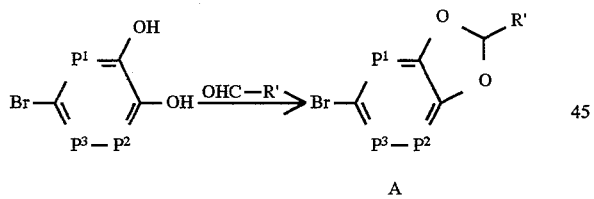

Scheme F:

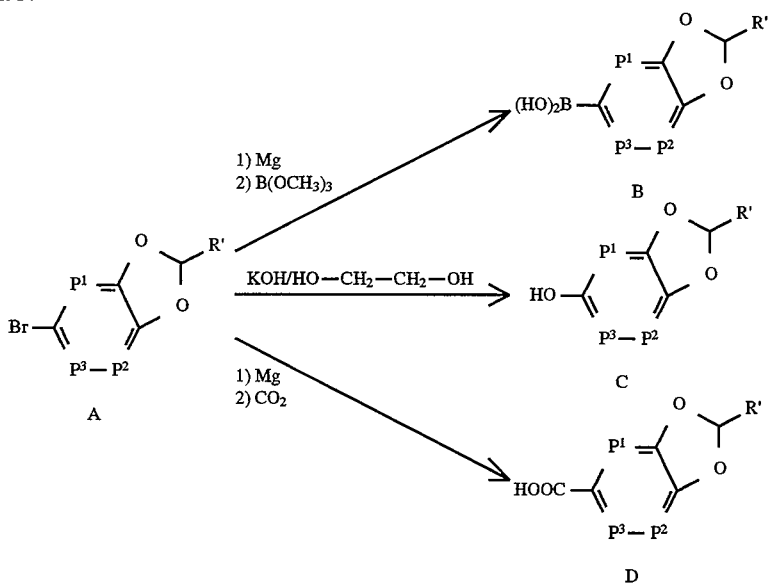

In schemes A to F, R' is (—M³)$_e$(—A³)$_f$(—M⁴)$_g$(—A⁴)$_h$—R*, where R* can be the same as R² or a suitably protected precursor for the coupling of a chiral fragment. The reaction of the intermediates with R¹(—A¹)$_a$(—M¹)$_b$(—A²)$_c$(—M²)$_d$—L is carried out by customary processes known per se to the person skilled in the art. For example, A can be coupled to arylboronic acids with transition-metal catalysis in an inert solvent at a temperature of from −78° C. to 200° C. Likewise, the boronic acid B can be coupled to suitable aryl halides, where in this case d is 0 and L is halogen or OSO₂—C$_k$F$_{2k+1}$, in which k is an integer from 1 to 10. The preferred catalyst in couplings to boronic acids is palladium or a palladium compound. Examples of solvents used are ethers, alcohols, water and hydrocarbons, or mixtures thereof. Furthermore, C can be reacted with carboxylic acids under conditions known per se to give esters or with aliphatic or aromatic alcohols or phenols to give ethers. Analogously, D can be reacted with aliphatic or aromatic alcohols by methods known per se to give esters.

The systems containing two aliphatic five-membered rings on the aromatic six-membered ring can be prepared by processes known per se to the person skilled in the art analogously to the methods described hitherto.

The synthesis of the R¹(—A¹)$_g$(—M¹)$_b$(—A²)$_c$(M²)$_d$ or (—M³)$_e$(—A³)$_f$(—M⁴)$_g$(—A⁴)$_h$R² radical is carried out by methods known per se to the person skilled in the art.

The preparation is carried out under reaction conditions which are known and suitable for said reactions. Use may also be made here of variants which are known per se, but are not described here in greater detail.

For example, reference may be made to DE-A 23 44 732, 24 50 088, 24 29 093, 25 02 904, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; EP-A 309 514 for compounds containing 1,3,4-thiadiazole-2,5-diyl groups; WO-A 92/16500 for naphthalene-2,6-diyl groups; DE-A 37 10 890 for bicyclo[2.2.2]octane-1,4-diyl groups; K. Seto et ah, Journal of the Chemical Society, Chemical Communications 1988, 56, for dioxoborinane-2,5-diyl groups.

The preparation of disubstituted pyridines, disubstituted pyrazines, disubstituted pyrimidines and disubstituted pyridazines is also given, for example, in the corresponding volumes in the series "The Chemistry of Heterocyclic Compounds" by A. Weissberger and E. C. Taylor (Editors).

Dioxane derivatives are expediently prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures between about 20° C. and about 150° C., preferably between 80° C. and 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitriles or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group by a fluorine atom, for example by the methods of Balz and Schiemann.

As far as the linking of ring systems to one another is concerned, reference may be made, for example to: N. Miyaura, T. Yanagai and A. Suzuki in Synthetic Communications 11 (1981), 513–519 DE—C-39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 for the direct linking of aromatics and heteroaromatics; DE-A 32 01 721 for compounds containing —CH₂CH₂— bridges, and Koji Sero et al. in Liquid Crystals 8 (1990) 861–870 for compounds containing —C≡C— bridges.

Esters of the formula (I) can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known and can be prepared analogously to known processes.

Particularly suitable reactive derivatives of the said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This can then be reacted with the corresponding alkyl halide, sulfonate or dialkyl sulfate, expediently in an inert solvent, such as acetone, 1,2-dimethoxy-ethane, DMF or dimethylsulfoxide, or alternatively with an excess of aqueous or aqueous/alcoholic NaOH or KOH at temperatures between about 20° and 100° C.

Regarding the synthesis of specific radicals R$^1$ and R$^2$, reference may additionally be made, for example, to EP-A 0 355 008 for compounds containing silicon-containing side chains and to EP-A 0 292 954 and EP-A 0 398 155 for compounds containing cyclopropyl groups in the side chain.

The provision of compounds of the formula (I) very generally considerably broadens the range of liquid-crystalline substances which are suitable, from various application points of view, for the preparation of liquid-crystalline mixtures.

In this connection, the compounds of the formula (I) have a broad range of applications. Depending on the choice of substituents, they can be used as base materials from which liquid-crystalline phases are predominantly composed; however, compounds of the formula (I) can also be added to liquid-crystalline base materials from other classes of compound, in order, for example, to modify the dielectric and/or optical anisotropy of a dielectric of this type and/or to optimize its threshold voltage and/or its viscosity.

The invention also relates to the use of compounds of the formula (I) in liquid-crystal mixtures, preferably ferroelectric, nematic, antiferroelectric and ferrielectric mixtures, particularly preferably in ferroelectric and nematic mixtures, in particular in ferroelectric mixtures.

The invention furthermore relates to liquid-crystal mixtures, preferably ferroelectric and nematic mixtures, in particular ferroelectric mixtures, containing one or more compounds of the formula (I). The liquid-crystal mixtures according to the invention generally contain from 2 to 35, preferably from 2 to 25, particularly preferably from 2 to 20 components.

They generally contain from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures containing compounds of the formula (I) according to the invention are preferably selected from known compounds having smectic and/or nematic and/or cholesteric phases. These include, for example:

derivatives of phenylpyrimidine, as described, for example, in WO 86/06401 and U.S. Pat. No. 4,874,542, meta-substituted aromatic compounds having a six-membered ring, as described, for example, in German Patent Application P 42 22 565, silicon compounds, as described, for example, in EP-A 0 355 008, mesogenic compounds containing only one side chain as described in EP-A 0 541 081, hydroquinone derivatives, as described, for example, in German Patent Application P 4 243 705, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, and thiadiazoles as described, for example, in EP-B 309 514. Examples of suitable chiral, non-racemic dopes are:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, and optically active tetrahydrofuran-2-carboxylic esters, as described, for example, in EP-A 0 355 561.

Particularly preferred further components of the mixtures according to the invention are compounds of the formulae II to XVI:

A. Phenylpyrimidines of the formula (11)

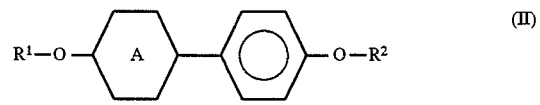

in which:

R$_1$ and R$_2$ are identical or different and are a straight-chain or branched alkyl group having 1 to 18 or 3 to 18 carbon atoms respectively, where a —CH$_2$— group adjacent to the oxygen in one or both of the radicals R$^1$ and R$^2$ may also be replaced by —CO—; and (III),

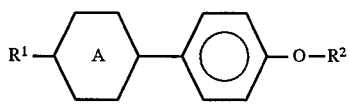 (III)

in which:
R₁ and R₂ are identical or different and are a branched or unbranched alkyl group having 1 to 18 or 3 to 18 carbon atoms respectively, where a —CH₂— group adjacent to the oxygen may also be replaced by —CO—;

B. Metasubstituted aromatic compounds having a six-membered ring, of the formula (IV)

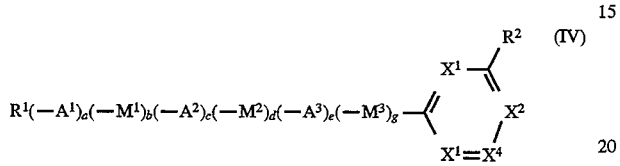 (IV)

in which
R¹ and R² are identical or different and are a straight-chain or branched alkyl radical having 1 to 22 or 3 to 22 carbon atoms respectively, where one or two non-adjacent —CH₂— groups may also be replaced by —O—, —CO—, —CO—O—, —O—CO—, —O—CO—O— or —Si(CH₃)₂—;

A¹, A² and A³ are identical or different and are 1,4-phenylene, in which one or two H atoms may be replaced by F, pyridine-2,5-diyl, in which one, two or three H atoms may be replaced by F, pyrimidine-2,5-diyl, in which one or two H atoms may be replaced by F, trans-1,4-cyclohexylene, in which one or two H atoms may be replaced by —CN and/or —CH₃, or 1,3,4-thiadiazole-2,5-diyl;

and A¹ is alternatively

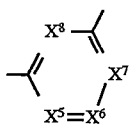

M¹, M² and M³ are identical or different and are —O—, —CO—O—, —O—CO—, —CH₂—O—, —O—CH₂— or —CH₂—CH₂—;

X¹, X², X³, X⁴, X⁵, X⁶, X⁷ and X⁸ are identical or different and are =CH—, =CF— or =N—, where the number of N atoms per six-membered ring is 0, 1 or 2, and a, b, c, d, e and f are zero or one, with the proviso that the sum a+c+e is 0, 1 or 2.

C. Carbonates of the formula (V)

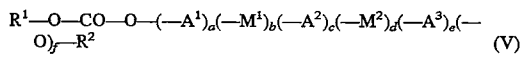 (V)

in which
R¹ and R² are identical or different and are a straight-chain or branched alkyl group having 1 to 22 or 3 to 22 carbon atoms respectively;

A¹, A² and A³ are identical or different and are 1,4-phenylene, in which one, two or three H atoms may also be replaced by F, pyrimidine-2,5-diyl, in which one or two H atoms may also be replaced by F, or pyridine-2,5-diyl, in which one or two H atoms may also be replaced by F;

M¹ and M² are identical or different and are —O—, —CO—, —CO—O—, —O—CO—, —CH₂—O—, —O—CH₂— or —CH₂—CH₂—;

a, b, c, d, e and f are zero or one, with the proviso that the sum a+c+e is 1,2 or 3.

D. Silicon compounds of the formula (VI)

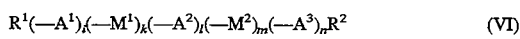 (VI)

in which
R¹ is a straight-chain or branched alkyl group having 1 to 22 or 3 to 22 carbon atoms respectively, where one or two non-adjacent —CH₂— groups may also be replaced by —O—, —CO—, —CO—O—, —O—CO— or —O—CO—O—;

R² is straight-chain or branched alkyl having 1 to 22 or 3 to 22 carbon atoms respectively, where one or two non-adjacent —CH₂— groups may also be replaced by —O—, —CO—, —CO—O—, —O—CO— or —O—CO—O—, with the proviso that one —CH₂— group not bonded to oxygen has been replaced by —Si(CH₃)₂—;

A¹, A² and A³ are identical or different and are 1,4-phenylene, in which one, two or three H atoms may be replaced by F, trans-1,4-cyclohexylene, pyridine-2,5-diyl, in which one or two H atoms may be replaced by F, pyrimidine-2,5-diyl, in which one or two H atoms may each be replaced by F, or 1,3,4-thiadiazole-2,5-diyl;

M¹ and M² are identical or different and are —CO—O—, —O—CO—, —CH₂—O— or —O—CH₂—, and i, k, l, m and n are zero or 1, with the proviso that i+l+n=2 or 3.

E. Hydroquinone derivatives of the formula (VII).

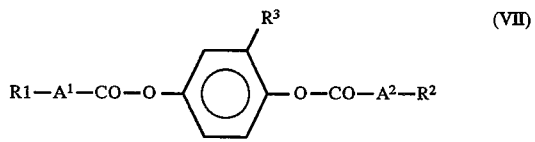 (VII)

in which
R¹ and R² are identical or different and are a straight-chain or branched alkyl radical having 1 or 3 to 16, preferably 1 or 3 to 10 carbon atoms respectively, where one or two non-adjacent —CH₂— groups may also be replaced by —O—, —CO—, —O—CO—, —CO—O— or —O—CO—O—, R³ is —CH₃, —CF₃ or —C₂H₅, A¹ and A² are identical or different and are

F. Pyridylpyrimidines of the formula (VIII)

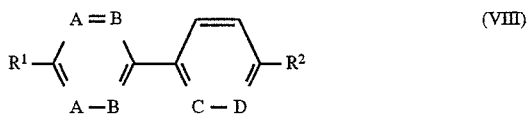

in which

A is N and B is CH or A is CH and B is N, C is N and D is CH or C is CH and D is N, where one or two CH groups may be replaced by CF groups, and $R^1$ and $R^2$ are identical or different and are a straight-chain or branched alkyl radical having 1 to 22 or 3 to 22 carbon atoms respectively, where one or two non-adjacent —$CH_2$— groups may also be replaced by —O—, —CO—, —CO—O—, —O—CO— or —O—CO—O—.

G. Phenylbenzoates of the formula (IX)

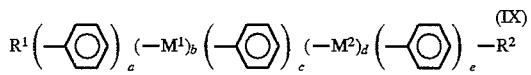

in which $R^1$ and $R^2$ are identical or different and are a straight-chain or branched alkyl radical having 1 to 22 or 3 to 22 carbon atoms respectively, where one or two non-adjacent —$CH_2$— groups may also be replaced by —O—, —CO—, —CO—O—, —O—CO— or —O—CO—O—;

$M^1$ and $M^2$ are identical or different and are —CO—O— or —O—CO—, and a, b, c, d and e are zero or one, with the proviso that a+c+e =2 or 3 and b+d=1 or 2.

H. Compounds containing only one side chain of the formula (X)

$R^1(-A^1)_a(-M^1)_b(-A^2)_c(-M^2)_d(-A^3)_e(-M^3)_f(-A^4)-H$ (X)

in which $R^1$ is a straight-chain or branched alkyl radical having 1 to 22 or 3 to 22 carbon atoms respectively, where one or two non-adjacent —$CH_2$— groups may also be replaced by —O—, —CO—, —CO—O—, —O—CO—, —O—CO—O— or —Si(CH$_3$)$_2$—;

$A^1$, $A^2$, $A^3$ and $A^4$ are identical or different and are 1,4-phenylene, in which one, two or three H atoms may be replaced by F or CN, pyridine-2,5-diyl, in which one or two H atoms may be replaced by F, pyrimidine-2,5-diyl, in which one or two H atoms may be replaced by F, trans-1,4-cyclohexylene, 1,3,4-thiadiazole-2,5-diyl or naphthalene-2,6-diyl;

$M^1$, $M^2$ and $M^3$ are identical or different and are —CO—O—, —O—CO—, —CH$_2$—O—, —O—CH$_2$— or —CH$_2$—CH$_2$—;

a, b, c, d, e and f are zero or one, with the proviso that the sum a+c+e is 0, 1, 2 or 3.

I. Optically active phenylbenzoates of the formula (XI)

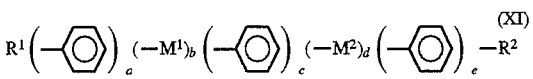

in which $R^1$ and $R^2$ are identical or different and are a straight-chain or branched alkyl radical having 1 to 22 or 3 to 22 carbon atoms respectively, where one or two non-adjacent —$CH_2$— groups may also be replaced by —O—, —CO—, —CO—O—, —O—CO— or —O—CO—O—, and in which at least one of the radicals $R^1$ and $R^2$ is chiral and non-racemic;

$M^1$ and $M^2$ are identical or different and are —CO—O—, —O—CO— or a single bond, and a, b, c, d and e are zero or one, with the proviso that a+c+e is 2 or 3.

J. Optically active oxirane ethers of the formula (XII)

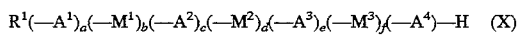

in which the symbols and indices have the following meaning:

* is a chiral center;

$R^1$ is a straight-chain or branched alkyl radical having 1 to 22 or 3 to 22 carbon atoms respectively, where one or two non-adjacent —$CH_2$— groups may also be replaced by —O—, —CO—, —CO—O—, —O—CO—, —O—CO—O— or —Si(CH$_3$)$_2$—, or the following optically active group:

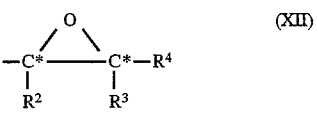

$R^2$, $R^3$, $R^4$, $R^5$, $R^6$ and $R^7$ are identical or different and are H or a straight-chain or branched alkyl radical having 1 to 16 or 3 to 16 carbon atoms respectively;

P is —$CH_2$— or —CO—;

$A^1$, $A^2$ and $A^3$ are identical or different and are 1,4-phenylene, in which one, two or three H atoms may be replaced by F, pyridine-2,5-diyl, in which one or two H atoms may each be replaced by F, pyrimidine-2,5-diyl, in which one or two H atoms may be replaced by F, trans-1,4-cyclohexylene, in which one or two H atoms may be replaced by —CN and/or —$CH_3$, or 1,3,4-thiadiazole-2,5-diyl;

$M^1$ and $M^2$ are identical or different and are —CO—O—, —O—CO—, —$CH_2$—O—, —O—$CH_2$— or —$CH_2$—$CH_2$—, and a, b, c, d and e are zero or 1.

K. Optically active oxirane esters of the formula (XIII)

$$R^1(-A^1)_a(-M^1)_b(-A^2)_c(-M^2)_d(-A^3)_e-O-CO-\underset{R^2}{C^*}\underset{R^3}{\overset{O}{-}}\underset{R^3}{C^*}\overset{R^4}{}$$ (XIII)

where the symbols and indices have the following meaning:

* is a chiral center;
  $R^1$ is a straight-chain or branched alkyl radical having 1 to 22 or 3 to 22 carbon atoms respectively, where one or two non-adjacent —$CH_2$— groups may also be replaced by —O—, —CO—, —CO—O—, —O—CO—, —O—CO—O— or —$Si(CH_3)_2$—;
  $R^2$, $R^3$ and $R^4$ are identical or different and are H or a straight-chain or branched alkyl radical having 1 to 16 carbon atoms;
  $A^1$, $A^2$ and $A^3$ are identical or different and are 1,4-phenylene, in which one, two or three H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —$CH_3$, or 1,3,4-thiadiazole-2,5-diyl;
  $M^1$ and $M^2$ are identical or different and are —CO—O—, —O—CO—, —$CH_2$—O—, —O—$CH_2$— or —$CH_2$—$CH_2$—;
  a, b, c, d and e are zero or one.

L. Optically active dioxolane ethers of the formula (XIV)

$$R^1(-A^1)_a(-M^1)_b(-A^2)_c(-M^2)_d(-A^3)_e-O-CH_2\underset{R^4}{\overset{O\overset{R^2}{\underset{R^3}{\diagup}}}{\diagdown\;\;\;\;\;O\diagup}}$$ (XIV)

where the symbols and indices have the following meanings:

* is a chiral center;
  $R^1$ is a straight-chain or branched alkyl radical having 1 to 22 or 3 to 22 carbon atoms respectively, where one or two non-adjacent —$CH_2$— groups may also be replaced by —O—, —CO—, —CO—O—, —O—CO—, —O—CO—O— or —$Si(CH_3)_2$—;
  $R^2$, $R^3$ and $R^4$ are identical or different and are H or a straight-chain or branched alkyl radical having 1 to 16 carbon atoms, where $R^2$ and $R^3$ together may alternatively be —$(CH_2)_5$— or —$(CH_2)_4$—;
  $A^1$, $A^2$ and $A^3$ are identical or different and are 1,4-phenylene, in which one, two or three H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —$CH_3$, or 1,3,4-thiadiazole-2,5-diyl;
  $M^1$ and $M^2$ are identical or different and are —CO—O—, —O—CO—, —$CH_2$—O—, —O—$CH_2$— or —$CH_2$—$CH_2$—, and
  a, b, c, d and e are zero or one.

M. Optically active dioxolane esters of the formula (XV)

$$R^1(-A^1)_a(-M^1)_b(-A^2)_c(-M^2)_d(-A^3)_e-O-CO-\underset{R^4}{\overset{O\overset{R_2\;\;\;R_3}{\underset{}{\diagup}}}{\diagdown\;\;\;\;\;O\diagup}}$$ (XV)

in which
  $R^1$ is a straight-chain or branched alkyl radical having 1 to 16 carbon atoms where one or more non-adjacent —$CH_2$— groups may be replaced by —O—, —CO—, —O—CO— or —CO—O—;
  $R^2$, $R^3$ and $R^4$ are identical or different and are H or a straight-chain alkyl radical having 1 to 16 carbon atoms, where $R^2$ and $R^3$ together may alternatively be —$(CH_2)_5$— or —$(CH_2)_4$—;
  $A^1$, $A^2$ and $A^3$ are identical or different and are 1,4-phenylene, in which one, two or three H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or—$CH_3$, or 1,3,4-thiadiazole-2,5-diyl;
  $M^1$ and $M^2$ are identical or different and are —CO—O—, —O—CO—, —$CH_2$—O—, —O—$CH_2$— or —$CH_2$—$CH_2$—, and
  a, b, c, d and e are zero or one.

N. Macrocyclic compounds of the formula (XVI)

(XVI)

where
  n is 0 or 1, and
  Y is —CO-(t-butyl) or—CO-(adamantyl).

The mixtures according to the invention are suitable for use in all areas of optical technology, for example in switching and display elements, light valves and components having NLO properties. The mixtures according to the invention are particularly suitable for use where the properties of smectic liquid crystals are utilized.

Achiral and chiral base compounds may be used in all areas in which anisotropic fluids are employed, for example as column material for gas chromatography.

Liquid-crystalline mixtures containing compounds of the formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1987).

Ferroelectric mixtures according to the invention are preferably used in the FLC cells described in the introduction, which are based on the utilization of the SSFLC effect (see, for example, J. W. Goodby et ah, Ferroelectric Liquid Crystals, 24 ff., Gordon & Breach, Philadelphia, 1991).

In these cells, the mixtures according to the invention are preferably employed in combinations with alignment layers, as proposed, for example, in DE-A 42 12 893 or in German Patent Application P 43 05 970 with the title "Cyclische Strukturelemente enthaltende Silan-Koppler als Orientierungsschichten" [Silane couplers containing cyclic structural elements as alignment layers], where an alignment film for liquid crystals is described which comprises a quasi-monomolecular layer of compounds of the formula

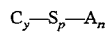

in which $C_y$ is a mediocyclic or macrocyclic carbon ring having 8 or more ring members, where this ring may also contain fused benzene rings and —O—, —N—, —S—, —Si— and —B— as hetero atoms;

$S_p$ is an alkyl group having 1 to 20 carbon atoms in which one or more non-adjacent —CH$_2$— groups may be replaced by —O—, —CO—, —O—CO—, —NH—CO—, —O—COO—, —NH—CO—NH—, —NH—CO—O—, —SO$_2$—, —Si(CH$_3$)$_2$—, —CH=CH— or —C≡C—;

$A_n$ is $SiX^1X^2X^3$, where $X^1$ is a single bond and $X^2$ and $X^3$ are identical or different and are a single bond, an alkyl group or an alkoxy group;

where the compounds are bonded to an oxygen-containing layer via the single bond(s) of the group $A_n$.

The mixtures according to the invention are furthermore suitable for field treatment, i.e. for operation in the quasi-bookshelf geometry (QBG) (see, for example, H. Rieger et al., SID 91 Digest (Anaheim), 1991, p. 396).

The mixtures according to the invention are likewise suitable for use in ferroelectric liquid-crystal displays which are based on utilization of the DHF effect or the PSFLCD effect (pitch stabilized ferroelectric liquid-crystal display, also known as SBF, short pitch bistable ferroelectric effect).

The invention is described in greater detail by means of the examples, but this is not intended to represent a limitation.

EXAMPLES

The phase-transition temperatures were determined from the changes in structure on heating with the aid of a polarizing microscope. By contrast, the melting point was determined using a DSC instrument. The phase-transition temperature data between the phases

| isotropic | (I) |
|---|---|
| nematic | (N or N*) |
| smetic C | (S$_C$ or S$_C$*) |
| smetic A | (S$_A$) |
| crystalline | (X) |
| glass transition | (Tg) | are given in °C., and the values are between the phase designations in the phase sequence.

Example 1

5-(2-Octyl-benzo[1,3]dioxol-5-yl)-2-octyloxypyridine 5 mmol of 2-octyl-benzo[1,3]dioxole-5-boronic acid and 5 mmol of 5-bromo-2-octyloxypyridine are introduced into a mixture of 30 ml of toluene, 15 ml of ethanol and 15 ml of water. 0.05 mmol of tetrakis(triphenylphosphine)palladium(O) and 12 mmol of sodium carbonate are added, and the mixture is refluxed for 6 hours. The phases are separated, the aqueous phase is extracted with tert-butyl methyl ether, and the combined organic phases are dried by means of Na$_2$SO$_4$. For further purification, the substance is chromatographed on silica gel.

The following compounds are prepared analogously:

Example 2

5-(2-Heptylbenzo[1,3]dioxol-5-yl)-2-heptylpyridine

Example 3

5-(2-Heptylbenzo[1,3]dioxol-5-yl)-2-(6-cyclopropylhexyloxy)pyridine

Example 4

5-(2-Heptylbenzo[1,3]dioxol-5-yl)-2-(9-cyclopropylnonyl)pyridine

Example 5

5-(2-Heptylbenzo[1,3]dioxol-5-yl)-2-(perfluoro-1H,1H-heptyloxy)pyridine

Example 6

5-(2-Heptylbenzo[1,3]dioxol-5-yl)-2-(5-oxanonyloxy)pyridine

Example 7

5-(2-Heptylbenzo[1,3]dioxol-5-yl)-2-(5-oxaundecyl)pyridine

Example 8

5-(2-Heptylbenzo[1,3]dioxol-5-yl)-2-(6-dimethylsila)decyloxypyridine

Example 9

5-(2-Heptylbenzo[1,3]dioxol-5-yl)-2-(9-dimethylsila)tetradecylpyridine

Example 10

5-(2-Heptylbenzo[1,3]dioxol-5-yl)-2-(pentylcarbonyloxy)pyridine

Example 11

5-(2-(9-Cyclopropylnonyl)benzo[1,3]dioxol-5-yl)-2-octyloxypyridine

Example 12

5-(2-(9-Cyclopropylnonyl)benzo[1,3]dioxol-5-yl)-2-heptylpyridine

Example 13

5-(2-(9-Cyclopropylnonyl)benzo[1,3]dioxol-5-yl)-2-(6-cyclopropylhexyloxy)pyridine

Example 14

5-(2-(9-Cyclopropylnonyl)benzo[1,3]dioxol-5-yl)-2-(9-cyclopropylnonyl)pyridine

Example 15

5-(2-(9-Cyclopropylnonyl)benzo[1,3]dioxol-5-yl)-2-(perfluoro-1H,1H-heptyloxy)pyridine

Example 16

5-(2-(9-Cyclopropylnonyl)benzo[1,3]dioxol-5-yl)-2-(5-oxanonyloxy)pyridine

Example 17

5-(2-(9-Cyclopropylnonyl)benzo[1,3]dioxol-5-yl)-2-(5-oxaundecyl)pyridine

Example 18

5-(2-(9-Cyclopropylnonyl)benzo[1,3]dioxol-5-yl)-2-(6-dimethylsila)decyloxypyridine

Example 19

5-(2-(9-Cyclopropylnonyl)benzo[1,3]dioxol-5-yl)-2-(9-dimethylsila)tetradecylpyridine

Example 20

5-(2-(9-Cyclopropylnonyl)benzo[1,3]dioxol-5-yl)-2-(pentylcarbonyloxy)pyridine

Example 21

5-(2-(Perfluoro-1H,1H-heptyl)benzo[1,3]dioxol-5-yl)-2-octyloxypyridine

Example 22

5-(2-(Perfluoro-1H,1H-heptyl)benzo[1,3]dioxol-5-yl)-2-heptylpyridine

Example 23

5-(2-(Perfluoro-1H,1H-heptyl)benzo[1,3]dioxol-5-yl)-2-(6-cyclopropylhexyloxy)pyridine

Example 24

5-(2-(Perfluoro-1H,1H-heptyl)benzo[1,3]dioxolo-5-yl)-2-(9-cyclopropylnonyl)pyridine

Example 25

5-(2-(Perfluoro-1H,1H-heptyl)benzo[1,3]dioxol-5-yl)-2-(perfluoro-1H,1H-heptyloxy)pyridine

Example 26

5-(2-(Perfluoro-1H,1H-heptyl)benzo[1,3]dioxol-5-yl)-2-(5-oxanonyloxy)pyridine

Example 27

5-(2-(Perfluoro-1H,1H-heptyl)benzo[1,3]dioxol-5-yl)-2-(5-oxaundecyl)pyridine

Example 28

5-(2-(Perfluoro-1H,1H-heptyl)benzo[1,3]dioxol-5-yl)-2-(6-dimethylsila)decyloxypyridine

Example 29

5-(2-(Perfluoro-1H,1H-heptyl)benzo[1,3]dioxol-5-yl)-2-(9-dimethylsila)tetradecylpyridine

Example 30

5-(2-(Perfluoro-1H,1H-heptyl)benzo[1,3]dioxol-5-yl)-2-(pentylcarbonyloxy)pyridine

Example 31

5-(2-(5-Oxaundecyl)benzo[1,3]dioxol-5-yl)-2-octyloxypyridine

Example 32

5-(2-(5-Oxaundecyl)benzo[1,3]dioxol-5-yl)-2-heptylpyridine

Example 33

5-(2-(5-Oxaundecyl)benzo[1,3]dioxol-5-yl)-2-(6-cyclopropylhexyloxy)pyridine

Example 34

5-(2-(5-Oxaundecyl)benzo[1,3]dioxol-5-yl)-2-(9-cyclopropylnonyl)pyridine

Example 35

5-(2-(5-Oxaundecyl)benzo[1,3]dioxol-5-yl)-2-(perfluoro-1H,1H-heptyloxy)pyridine

Example 36

5-(2-(5-Oxaundecyl)benzo[1,3]dioxol-5-yl)-2-(5-oxanonyloxy)pyridine

Example 37

5-(2-(5-Oxaundecyl)benzo[1,3]dioxol-5-yl)-2-(5-oxaundecyl)pyridine

Example 38

5-(2-(5-Oxaundecyl)benzo[1,3]dioxol-5-yl)-2-(6-dimethylsila)decyloxypyridine

Example 39

5-(2-(5-Oxaundecyl)benzo[1,3]dioxol-5-yl)-2-(9-dimethylsila)tetradecylpyridine

Example 40

5-(2-(5-Oxaundecyl)benzo[1,3]dioxol-5-yl)-2-(pentylcarbonyloxy)pyridine

Example 41
5-(2-(9-Dimethylsila)tetradecylbenzo[1,3]dioxol-5-yl)-2-octyloxypyridine

Example 42
5-(2-(9-Dimethylsila)tetradecylbenzo[1,3]dioxol-5-yl)-2-heptylpyridine

Example 43
5-(2-(9-Dimethylsila)tetradecylbenzo[1,3]dioxol-5-yl)-2-(6-cyclopropylhexyloxy)pyridine

Example 44
5-(2-(9-Dimethylsila)tetradecylbenzo[1,3]dioxol-5-yl)-2-(9-cyclopropylnonyl)pyridine

Example 45
5-(2-(9-Dimethylsila)tetradecylbenzo[1,3]dioxol-5-yl)-2-(perfluoro-1H,1H-heptyloxy)pyridine

Example 46
5-(2-(9-Dimethylsila)tetradecylbenzo[1,3]dioxol-5-yl)-2-(5-oxanonyloxy)pyridine

Example 47
5-(2-(9-Dimethylsila)tetradecylbenzo[1,3]dioxol-5-yl)-2-(5-oxaundecyl)pyridine

Example 48
5-(2-(9-Dimethylsila)tetradecylbenzo[1,3]dioxol-5-yl)-2-(6-dimethylsila)decyloxypyridine

Example 49
5-(2-(9-Dimethylsila)tetradecylbenzo[1,3]dioxol-5-yl)-2-(9-dimethylsila)tetradecylpyridine

Example 50
5-(2-(9-Dimethylsila)tetradecylbenzo[1,3]dioxol-5-yl)-2-(pentylcarbonyloxy)pyridine

Example 51
2-(2-Heptylbenzo[1,3]dioxol-5-yl)-5-(4-octyloxyphenyl)pyrimidine

Example 52
2-(2-Heptylbenzo[1,3]dioxol-5-yl)-5-(4-heptylphenyl)pyrimidine

Example 53
2-(2-Heptylbenzo[1,3]dioxol-5-yl)-5-(4-(6-cyclopropylhexyloxy)phenyl)pyrimidine

Example 54
2-(2-Heptylbenzo[1,3]dioxol-5-yl)-5-(4-(9-cyclopropylnonyl)phenyl)pyrimidine

Example 55
2-(2-Heptylbenzo[1,3]dioxol-5-yl)-5-(4-(perfluoro-1H,1H-heptyloxy)phenyl)pyrimidine

Example 56
2-(2-Heptylbenzo[1,3]dioxol-5-yl)-5-(4-(5-oxanonyloxy)phenyl)pyrimidine

Example 57
2-(2-Heptylbenzo[1,3]dioxol-5-yl)-5-(4-(5-oxaundecyl)phenyl)pyrimidine

Example 58
2-(2-Heptylbenzo[1,3]dioxol-5-yl)-5-(4-(6-dimethylsila)decyloxyphenyl)pyrimidine

Example 59
2-(2-Heptylbenzo[1,3]dioxol-5-yl)-5-(4-(9-dimethylsila)tetradecylphenyl)pyrimidine

Example 60
2-(2-Heptylbenzo[1,3]dioxol-5-yl)-5-(4-(pentylcarbonyloxy)phenyl)pyrimidine

Example 61
2-(2-(9-Cyclopropylnonyl)benzo[1,3]dioxol-5-yl)-5-(4-octyloxyphenyl)pyrimidine

Example 62
2-(2-(9-Cyclopropylnonyl)benzo[1,3]dioxol-5-yl)-5-(4-heptylphenyl)pyrimidine

Example 63
2-(2-(9-Cyclopropylnonyl)benzo[1,3]dioxol-5-yl)-5-(4-(6-cyclopropylhexyloxy)phenyl)pyrimidine

Example 64
2-(2-(9-Cyclopropylnonyl)benzo[1,3]dioxol-5-yl)-5-(4-(9-cyclopropylnonyl)phenyl)pyrimidine

Example 65
2-(2-(9-Cyclopropylnonyl)benzo[1,3]dioxol-5-yl)-5-(4-(perfluoro-1H,1H-heptyloxy)phenyl)pyrimidine

Example 66
2-(2-(9-Cyclopropylnonyl)benzo[1,3]dioxol-5-yl)-5-(4-(5-oxanonyloxylphenyl)pyrimidine

Example 67
2-(2-(9-Cyclopropylnonyl)benzo[1,3]dioxol-5-yl)-5-(4-(5-oxaundecyl)phenyl)pyrimidine

Example 68
2-(2-(9-Cyclopropylnonyl)benzo[1,3]dioxol-5-yl)-5-(4-(6-dimethylsila)decyloxyphenyl)pyrimidine

Example 69
2-(2-(9-Cyclopropylnonyl)benzo[1,3]dioxol-5-yl)-5-(4-(9-dimethylsila)tetradecylphenyl)pyrimidine

Example 70
2-(2-(9-Cyclopropylnonyl)benzo[1,3]dioxol-5-yl)-5-(4-(pentylcarbonyloxy)phenyl)pyrimidine

Example 71

2-(2-(Perfluoro-1H,1H-heptyl)benzo[1,3]dioxol-5-yl)-5-(4-octyloxyphenyl)pyrimidine

Example 72

2-(2-(Perfluoro-1H,1H-heptyl)benzo[1,3]dioxol-5-yl)-5-(4-heptylphenyl)pyrimidine

Example 73

2-(2-(Perfluoro-1H,1H-heptyl)benzo[1,3]dioxol-5-yl)-5-(4-(6-cyclopropylhexyloxy)phenyl)pyrimidine

Example 74

2-(2-(Perfluoro-1H,1H-heptyl)benzo[1,3]dioxol-5-yl)-5-(4-(9-cyclopropylnonyl)phenyl)pyrimidine

Example 75

2-(2-(Perfluoro-1H,1H-heptyl)benzo[1,3]dioxol-5-yl)-5-(4-(perfluoro-1H,1H-heptyloxy)phenyl)pyrimidine

Example 76

2-(2-(Perfluoro-1H,1H-heptyl)benzo[1,3]dioxol-5-yl)-5-(4-(5-oxanonyloxy)phenyl)pyrimidine

Example 77

2-(2-(Perfluoro-1H,1H-heptyl)benzo[1,3]dioxol-5-yl)-5-(4-(5-oxaundecyl)phenyl)pyrimidine

Example 78

2-(2-(Perfluoro-1H,1H-heptyl)benzo[1,3]dioxol-5-yl)-5-(4-(6-dimethylsila)decyloxyphenyl)pyrimidine

Example 79

2-(2-(Perfluoro-1H,1H-heptyl)benzo[1,3]dioxol-5-yl)-5-(4-(9-dimethylsila)tetradecylphenyl)pyrimidine

Example 80

2-(2-(Perfluoro-1H,1H-heptyl)benzo[1,3]dioxol-5-yl)-5-(4-(1-(pentylcarbonyloxy)phenyl)pyrimidine

Example 81

2-(2-(5-Oxaundecyl)benzo[1,3]dioxol-5-yl)-5-(4-octyloxyphenyl)pyrimidine

Example 82

2-(2-(5-Oxaundecyl)benzo[1,3]dioxol-5-yl)-5-(4-heptylphenyl)pyrimidine

Example 83

2-(2-(5-Oxaundecyl)benzo[1,3]dioxol-5-yl)-5-(4-(6-cyclopropylhexyloxy)phenyl)pyrimidine

Example 84

2-(2-(5-Oxaundecyl)benzo[1,3]dioxol-5-yl)-5-(4-(9-cyclopropylnonyl)phenyl)pyrimidine

Example 85

2-(2-(5-Oxaundecyl)benzo[1,3]dioxol-5-yl)-5-(4-(perfluoro-1H,1H-heptyloxy)phenyl)pyrimidine

Example 86

2-(2-(5-Oxaundecyl)benzo[1,3]dioxol-5-yl)-5-(4-(5-oxanonyloxy)phenyl)pyrimidine

Example 87

2-(2-(5-Oxaundecyl)benzo[1,3]dioxol-5-yl)-5-(4-(5-oxaundecyl)phenyl)pyrimidine

Example 88

2-(2-(5-Oxaundecyl)benzo[1,3]dioxol-5-yl)-5-(4-(6-dimethylsila)decyloxyphenyl)pyrimidine

Example 89

2-(2-(5-Oxaundecyl)benzo[1,3]dioxol-5-yl)-5-(4-(9-dimethylsila)tetradecylphenyl)pyrimidine

Example 90

2-(2-(5-Oxaundecyl)benzo[1,3]dioxol-5-yl)-5-(4-(pentylcarbonyloxy)phenyl)pyrimidine

Example 91

2-(2-(9-Dimethylsila)tetradecylbenzo[1,3]dioxol-5-yl)-5-(4-octyloxyphenyl)pyrimidine

Example 92

2-(2-(9-Dimethylsila)tetradecylbenzo[1,3]dioxol-5-yl)-5-(4-heptylphenyl)pyrimidine

Example 93

2-(2-(9-Dimethylsila)tetradecylbenzo[1,3]dioxol-5-yl)-5-(4-(6-cyclopropylhexyloxy)phenyl)pyrimidine

Example 94

2-(2-(9-Dimethylsila)tetradecylbenzo[1,3]dioxol-5-yl)-5-(4-(9-cyclopropylnonyl)phenyl)pyrimidine

Example 95

2-(2-(9-Dimethylsila)tetradecylbenzo[1,3]dioxol-5-yl)-5-(4-(perfluoro-1H,1H-heptyloxy)phenyl)pyrimidine

Example 96

2-(2-(9-Dimethylsila)tetradecylbenzo[1,3]dioxol-5-yl)-5-(4-(5-oxanonyloxy)phenyl)pyrimidine

Example 97

2-(2-(9-Dimethylsila)tetradecylbenzo[1,3]dioxol-5-yl)-5-(4-(5-oxaundecyl)phenyl)pyrimidine

Example 98

2-(2-(9-Dimethylsila)tetradecylbenzo[1,3]dioxol-5-yl)-5-(4-(6-dimethylsila)decyloxyphenyl)pyrimidine

Example 99

2-(2-(9-Dimethylsila)tetradecylbenzo[1,3]dioxol-5-yl)-5-(4-(9-dimethylsila)tetradecylphenyl)pyrimidine

Example 100

2-(2-(9-Dimethylsila)tetradecylbenzo[1,3]dioxol-5-yl)-5-(4-(pentylcarbonyloxy)phenyl)pyrimidine

Example 101

2-(2-Heptyl-3,3,4-trifluoro-2,3-dihydrobenzofuran-5-yl)-5-(4-octyloxyphenyl)pyrimidine

Example 102

2-(2-Heptyl-3,3,4-trifluoro-2,3-dihydrobenzofuran-5-yl)-5-(4-heptylphenyl)pyrimidine

Example 103

2-(2-Heptyl-3,3,4-trifluoro-2,3-dihydrobenzofuran-5-yl)-5-(4-(6-cyclopropylhexyloxy)phenyl)pyrimidine

Example 104

2-(2-Heptyl-3,3,4-trifluoro-2,3-dihydrobenzofuran-5-yl)-5-(4-(9-cyclopropylnonyl)phenyl)pyrimidine

Example 105

2-(2-Heptyl-3,3,4-trifluoro-2,3-dihydrobenzofuran-5-yl)-5-(4-(perfluoro-1H,1H-heptyloxy)phenyl)pyrimidine

Example 106

2-(2-Heptyl-3,3,4-trifluoro-2,3-dihydrobenzofuran-5-yl)-5-(4-(5-oxanonyloxy)phenyl)pyrimidine

Example 107

2-(2-Heptyl-3,3,4-trifluoro-2,3-dihydrobenzofuran-5-yl)-5-(4-(5-oxaundecyl)phenyl)pyrimidine

Example 108

2-(2-Heptyl-3,3,4-trifluoro-2,3-dihydrobenzofuran-5-yl)-5-(4-(6-dimethylsila)decyloxyphenyl)pyrimidine

Example 109

2-(2-Heptyl-3,3,4-trifluoro-2,3-dihydrobenzofuran-5-yl)-5-(4-(9-dimethylsila)tetradecylphenyl)pyrimidine

Example 110

2-(2-Heptyl-3,3,4-trifluoro-2,3-dihydrobenzofuran-5-yl)-5-(4-(pentylcarbonyloxy)phenyl)pyrimidine

Example 111

2-(2-(9-Cyclopropylnonyl)-3,3,4-trifluoro-2,3-dihydrobenzofuran-5-yl)-5-(4-octyloxyphenyl)pyrimidine

Example 112

2-(2-(9-Cyclopropylnonyl)-3,3,4-trifluoro-2,3-dihydrobenzofuran-5-yl)-5-(4-heptylphenyl)pyrimidine

Example 113

2-(2-(9-Cyclopropylnonyl)-3,3,4-trifluoro-2,3-dihydrobenzofuran-5-yl)-5-(4-(6-cyclopropylhexyloxy)phenyl)pyrimidine

Example 114

2-(2-(9-Cyclopropylnonyl)-3,3,4-trifluoro-2,3-dihydrobenzofuran-5-yl)-5-(4-(9-cyclopropylnonyl)phenyl)pyrimidine

Example 115

2-(2-(9-Cyclopropylnonyl)-3,3,4-trifluoro-2,3-dihydrobenzofuran-5-yl)-5-(4-(perfluoro-1H,1H-heptyloxy)phenyl)pyrimidine

Example 116

2-(2-(9-Cyclopropylnonyl)-3,3,4-trifluoro-2,3-dihydrobenzofuran-5-yl)-5-(4-(5-oxanonyloxy)phenyl)pyrimidine

Example 117

2-(2-(9-Cyclopropylnonyl)-3,3,4-trifluoro-2,3-dihydrobenzofuran-5-yl)-5-(4-(5-oxaundecyl)phenyl)pyrimidine

Example 118

2-(2-(9-Cyclopropylnonyl)-3,3,4-trifluoro-2,3-dihydrobenzofuran-5-yl)-5-(4-(6-dimethylsila)decyloxyphenyl)pyrimidine

Example 119

2-(2-(9-Cyclopropylnonyl)-3,3,4-trifluoro-2,3-dihydrobenzofuran-5-yl)-5-(4-(9-dimethylsila)tetradecylphenyl)pyrimidine

Example 120

2-(2-(9-Cyclopropylnonyl)-3,3,4-trifluoro-2,3-dihydrobenzofuran-5-yl)-5-(4-(pentylcarbonyloxy)phenyl)pyrimidine

Example 121

2-(2-(Perfluoro-1H,1H-heptyl)-3,3,4-trifluoro-2,3-dihydrobenzofuran-5-yl)-5-(4-octyloxyphenyl)pyrimidine

Example 122

2-(2-(Perfluoro-1H,1H-heptyl)-3,3,4-trifluoro-2,3-dihydrobenzofuran-5-yl)-5-(4-heptylphenyl)pyrimidine

Example 123

2-(2-(Perfluoro-1H,1H-heptyl)-3,3,4-trifluoro-2,3-dihydrobenzofuran-5-yl)-5-(4-(6-cyclopropylhexyloxy)phenyl)pyrimidine

Example 124

2-(2-(Perfluoro-1H,1H-heptyl)-3,3,4-trifluoro-2,3-dihydrobenzofuran-5-yl)-5-(4-(9-cyclopropylnonyl)phenyl)pyrimidine

Example 125

2-(2-(Perfluoro-1H,1H-heptyl)-3,3,4-trifluoro-2,3-dihydrobenzofuran-5-yl)-5-(4-(perfluoro-1H,1H-heptyloxy)phenyl)pyrimidine

Example 126

2-(2-(Perfluoro-1H,1H-heptyl)-3,3,4-trifluoro-2,3-dihydrobenzofuran-5-yl)-5-(4-(5-oxanonyloxy)phenyl)pyrimidine

Example 127

2-(2-(Perfluoro-1H,1H-heptyl)-3,3,4-trifluoro-2,3-dihydrobenzofuran-5-yl)-5-(4-(5-oxaundecyl)phenyl)pyrimidine

Example 128

2-(2-(Perfluoro-1H,1H-heptyl)-3,3,4-trifluoro-2,3-dihydrobenzofuran-5-yl)-5-(4-(6-dimethylsila)decyloxyphenyl)pyrimidine

Example 129

2-(2-(Perfluoro-1H,1H-heptyl)-3,3,4-trifluoro-2,3-dihydrobenzofuran-5-yl)-5-(4-(9-dimethylsila)tetradecylphenyl)pyrimidine

Example 130

2-(2-(Perfluoro-1H,1H-heptyl)-3,3,4-trifluoro-2,3-dihydrobenzofuran-5-yl)-5-(4-(pentylcarbonyloxy)phenyl)pyrimidine

Example 131

2-(2-(5-Oxaundecyl)-3,3,4-trifluoro-2,3-dihydrobenzofuran-5-yl)-5-(4-octyloxyphenyl)pyrimidine

Example 132

2-(2-(5-Oxaundecyl)-3,3,4-trifluoro-2,3-dihydrobenzofuran-5-yl)-5-(4-heptylphenyl)pyrimidine

Example 133

2-(2-(5-Oxaundecyl)-3,3,4-trifluoro-2,3-dihydrobenzofuran-5-yl)-5-(4-(6-cyclopropylhexyloxy)phenyl)pyrimidine

Example 134

2-(2-(5-Oxaundecyl)-3,3,4-trifluoro-2,3-dihydrobenzofuran-5-yl)-5-(4-(9-cyclopropylnonyl)phenyl)pyrimidine

Example 135

2-(2-(5-Oxaundecyl)-3,3,4-trifluoro-2,3-dihydrobenzofuran-5-yl)-5-(4-(perfluoro-1H,1H-heptyloxy)phenyl)pyrimidine

Example 136

2-(2-(5-Oxaundecyl)-3,3,4-trifluoro-2,3-dihydrobenzofuran-5-yl)-5-(4-(5-oxanonyloxy)phenyl)pyrimidine

Example 137

2-(2-(5-Oxaundecyl)-3,3,4-trifluoro-2,3-dihydrobenzofuran-5-yl)-5-(4-(5-oxaundecyl)phenyl)pyrimidine

Example 138

2-(2-(5-Oxaundecyl)-3,3,4-trifluoro-2,3-dihydrobenzofuran-5-yl)-5-(4-(6-dimethylsila)decyloxyphenyl)pyrimidine

Example 139

2-(2-(5-Oxaundecyl)-3,3,4-trifluoro-2,3-dihydrobenzofuran-5-yl)-5-(4-(9-dimethylsila)tetradecylphenyl)pyrimidine

Example 140

2-(2-(5-Oxaundecyl)-3,3,4-trifluoro-2,3-dihydrobenzofuran-5-yl)-5-(4-(pentylcarbonyloxy)phenyl)pyrimidine

Example 141

2-(2-(9-Dimethylsila)tetradecyl-3,3,4-trifluoro-2,3-dihydrobenzofuran-5-yl)-5-(4-octyloxyphenyl)pyrimidine

Example 142

2-(2-(9-Dimethylsila)tetradecyl-3,3,4-trifluoro-2,3-dihydrobenzofuran-5-yl)-5-(4-heptylphenyl)pyrimidine

Example 143

2-(2-(9-Dimethylsila)tetradecyl-3,3,4-trifluoro-2,3-dihydrobenzofuran-5-yl)-5-(4-(6-cyclopropylhexyloxy)phenyl)pyrimidine

Example 144

2-(2-(9-Dimethylsila)tetradecyl-3,3,4-trifluoro-2,3-dihydrobenzofuran-5-yl)-5-(4-(9-cyclopropylnonyl)phenyl)pyrimidine

Example 145

2-(2-(9-Dimethylsila)tetradecyl-3,3,4-trifluoro-2,3-dihydrobenzofuran-5-yl)-5-(4-(perfluoro-1H,1H-heptyloxy)phenyl)pyrimidine

Example 146

2-(2-(9-Dimethylsila)tetradecyl-3,3,4-trifluoro-2,3-dihydrobenzofuran-5-yl)-5-(4-(5-oxanonyloxy)phenyl)pyrimidine

Example 147

2-(2-(9-Dimethylsila)tetradecyl-3,3,4-trifluoro-2,3-dihydrobenzofuran-5-yl)-5-(4-(5-oxaundecyl)phenyl)pyrimidine

Example 148

2-(2-(9-Dimethylsila)tetradecyl-3,3,4-trifluoro-2,3-dihydrobenzofuran-5-yl)-5-(4-(6-dimethylsila)decyloxyphenyl)pyrimidine

Example 149

2-(2-(9-Dimethylsila)tetradecyl-3,3,4-trifluoro-2,3-dihydrobenzofuran-5-yl)-5-(4-(9-dimethylsila)tetradecylphenyl)pyrimidine

Example 150

2-(2-(9-Dimethylsila)tetradecyl-3,3,4-trifluoro-2,3-dihydrobenzofuran-5-yl)-5-(4-(pentylcarbonyloxy)phenyl)pyrimidine

Example 151

2-Heptyl-3,3-difluoro-5-[5-(4-octyloxyphenyl)pyrimidin-2-yl]-2,3-dihydrofuro[3,2-b]pyridine

Example 152

2-Heptyl-3,3-difluoro-5-[5-(4-heptylphenyl)pyrimidin-2-yl]-2,3-dihydrofuro[3,2-b]pyridine

Example 153

2-Heptyl-3,3-difluoro-5-[5-(4-(6-cyclopropylhexyloxy)phenyl)pyrimidin-2-yl]-2,3-dihydrofuro[3,2-b]pyridine

Example 154

2-Heptyl-3,3-difluoro-5-[5-(4-(9-cyclopropylnonyl)phenyl)pyrimidin-2-yl]-2,3-dihydrofuro[3,2-b]pyridine

Example 155

2-Heptyl-3,3-difluoro-5-[5-(4-(perfluoro-1H,1H-heptyloxy)phenyl)pyrimidin-2-yl]-2,3-dihydrofuro[3,2-b]pyridine

Example 156

2-Heptyl-3,3-difluoro-5-[5-(4-(5-oxanonyloxy)phenyl)pyrimidin-2-yl]-2,3-dihydrofuro[3,2-b]pyridine

Example 157

2-Heptyl-3,3-difluoro-5-[5-(4-(5-oxaundecyl)phenyl)pyrimidin-2-yl]-2,3-dihydrofuro[3,2-b]pyridine

Example 158

2-Heptyl-3,3-difluoro-5-[5-(4-(6-dimethylsila)decyloxyphenyl)pyrimidin-2-yl]-2,3-dihydrofuro[3,2-b]pyridine

Example 159

2-Heptyl-3,3-difluoro-5-[5-(4-(9-dimethylsila)tetradecylphenyl)pyrimidin-2-yl]-2,3-dihydrofuro[3,2-b]pyridine

Example 160

2-Heptyl-3,3-difluoro-5-[5-(4-(pentylcarbonyloxy)phenyl)pyrimidin-2-yl]-2,3-dihydrofuro[3,2-b]pyridine

Example 161

2-(9-Cyclopropylnonyl)-3,3-difluoro-5-[5-(4-octyloxyphenyl)pyrimidin-2-yl]-2,3-dihydrofuro[3,2-b]pyridine

Example 162

2-(9-Cyclopropylnonyl)-3,3-difluoro-5-[5-(4-heptylphenyl)pyrimidin-2-yl]-2,3-dihydrofuro[3,2-b]pyridine

Example 163

2-(9-Cyclopropylnonyl)-3,3-difluoro-5-[5-(4-(6-cyclopropylhexyloxy)phenyl)pyrimidin-2-yl]-2,3-dihydrofuro[3,2-b]pyridine

Example 164

2-(9-Cyclopropylnonyl)-3,3-difluoro-5-[5-(4-(9-cyclopropylnonyl)phenyl)pyrimidin-2-yl]-2,3-dihydrofuro[3,2-b]pyridine

Example 165

2-(9-Cyclopropylnonyl)-3,3-difluoro-5-[5-(4-(perfluoro-1H,1H-heptyloxy)phenyl)pyrimidin-2-yl]-2,3-dihydrofuro[3,2-b]pyridine

Example 166

2-(9-Cyclopropylnonyl)-3,3-difluoro-5-[5-(4-(5-oxanonyloxy)phenyl)pyrimidin-2-yl]-2,3-dihydrofuro[3,2-b]pyridine

Example 167

2-(9-Cyclopropylnonyl)-3,3-difluoro-5-[5-(4-(5-oxaundecyl)phenyl)pyrimidin-2-yl]-2,3-dihydrofuro[3,2-b]pyridine

Example 168

2-(9-Cyclopropylnonyl)-3,3-difluoro-5-[5-(4-(6-dimethylsila)decyloxyphenyl)pyrimidin-2-yl]-2,3-dihydrofuro[3,2-b]pyridine

Example 169

2-(9-Cyclopropylnonyl)-3,3-difluoro-5-[5-(4-(9-dimethylsila)tetradecylphenyl)pyrimidin-2-yl]-2,3-dihydrofuro[3,2-b]pyridine

Example 170

2-(9-Cyclopropylnonyl)-3,3-difluoro-5-[5-(4-(pentylcarbonyloxy)phenyl)pyrimidin-2-yl]-2,3-dihydrofuro[3,2-b]pyridine

Example 171

2-(Perfluoro-1H,1H-heptyl)-3,3-difluoro-5-[5-(4-octyloxyphenyl)pyrimidin-2-yl]-2,3-dihydrofuro[3,2-b]pyridine

Example 172

2-(Perfluoro-1H,1H-heptyl)-3,3-difluoro-5-[5-(4-heptylphenyl)pyrimidin-2-yl]-2,3-dihydrofuro[3,2-b]pyridine

Example 173

2-(Perfluoro-1H,1H-heptyl)-3,3-difluoro-5-[5-(4-(6-cyclopropylhexyloxy)phenyl)pyrimidin-2-yl]-2,3-dihydrofuro[3,2-b]pyridine

Example 174

2-(Perfluoro-1H,1H-heptyl)-3,3-difluoro-5-[5-(4-(9-cyclopropylnonyl)phenyl)pyrimidin-2-yl]-2,3-dihydrofuro[3,2-b]pyridine

Example 175

2-(Perfluoro-1H,1H-heptyl)-3,3-difluoro-5-[5-(4-(perfluoro-1H,1H-heptyloxy)phenyl)pyrimidin-2-yl]-2,3-dihydrofuro[3,2-b]pyridine

Example 176

2-(Perfluoro-1H,1H-heptyl)-3,3-difluoro-5-[5-(4-(5-oxanonyloxy)phenyl)pyrimidin-2-yl]-2,3-dihydrofuro[3,2-b]pyridine

Example 177

2-(Perfluoro-1H,1H-heptyl)-3,3-difluoro-5-[5-(4-(5-oxaundecyl)phenyl)pyrimidin-2-yl]-2,3-dihydrofuro[3,2-b]pyridine

Example 178

2-(Perfluoro-1H,1H-heptyl)-3,3-difluoro-5-[5-(4-(6-dimethylsila)decyloxyphenyl)pyrimidin-2-yl]-2,3-dihydrofuro[3,2-b]pyridine

Example 179

2-(Perfluoro-1H,1H-heptyl)-3,3-difluoro-5-[5-(4-(9-dimethylsila)tetradecylphenyl)pyrimidin-2-yl]-2,3-dihydrofuro[3,2-b]pyridine

Example 180

2-(Perfluoro-1H,1H-heptyl)-3,3-difluoro-5-[5-(4-(pentylcarbonyloxy)phenyl)pyrimidin-2-yl]-2,3-dihydrofuro[3,2-b]pyridine

Example 181

2-(5-Oxaundecyl)-3,3-difluoro-5-[5-(4-octyloxyphenyl)pyrimidin-2-yl]-2,3-dihydrofuro[3,2-b]pyridine

Example 182

2-(5-Oxaundecyl)-3,3-difluoro-5-[5-(4-heptylphenyl)pyrimidin-2-yl]-2,3-dihydrofuro[3,2-b]pyridine

Example 183

2-(5-Oxaundecyl)-3,3-difluoro-5-[5-(4-(6-cyclopropylhexyloxy)phenyl)pyrimidin-2-yl]-2,3-dihydrofuro[3,2-b]pyridine

Example 184

2-(5-Oxaundecyl)-3,3-difluoro-5-[5-(4-(9-cyclopropylnonyl)phenyl)pyrimidin-2-yl]-2,3-dihydrofuro[3,2-b]pyridine

Example 185

2-(5-Oxaundecyl)-3,3-difluoro-5-[5-(4-(perfluoro-1H,1H-heptyloxy)phenyl)pyrimidin-2-yl]-2,3-dihydrofuro[3,2-b]pyridine

Example 186

2-(5-Oxaundecyl)-3,3-difluoro-5-[5-(4-(5-oxanonyloxy)phenyl)pyrimidin-2-yl]-2,3-dihydrofuro[3,2-b]pyridine

Example 187

2-(5-Oxaundecyl)-3,3-difluoro-5-[5-(4-(5-oxaundecyl)phenyl)pyrimidin-2-yl]-2,3-dihydrofuro[3,2-b]pyridine

Example 188

2-(5-Oxaundecyl)-3,3-difluoro-5-[5-(4-(6-dimethylsila)decyloxyphenyl)pyrimidin-2-yl]-2,3-dihydrofuro[3,2-b]pyridine

Example 189

2-(5-Oxaundecyl)-3,3-difluoro-5-[5-(4-(9-dimethylsila)tetradecylphenyl)pyrimidin-2-yl]-2,3-dihydrofuro[3,2-b]pyridine

Example 190

2-(5-Oxaundecyl)-3,3-difluoro-5-[5-(4-(pentylcarbonyloxy)phenyl)pyrimidin-2-yl]-2,3-dihydrofuro[3,2-b]pyridine

Example 191

2-(9-Dimethylsila)tetradecyl-3,3-difluoro-5-[5-(4-octyloxyphenyl)pyrimidin-2-yl]-2,3-dihydrofuro[3,2-b]pyridine

Example 192

2-(9-Dimethylsila)tetradecyl-3,3-difluoro-5-[5-(4-heptylphenyl)pyrimidin-2-yl]-2,3-dihydrofuro[3,2-b]pyridine

Example 193

2-(9-Dimethylsila)tetradecyl-3,3-difluoro-5-[5-(4-(6-cyclopropylhexyloxy)phenyl)pyrimidin-2-yl]-2,3-dihydrofuro[3,2-b]pyridine

Example 194

2-(9-Dimethylsila)tetradecyl-3,3-difluoro-5-[5-(4-(9-cyclopropylnonyl)phenyl)pyrimidin-2-yl]-2,3-dihydrofuro[3,2-b]pyridine

Example 195

2-(9-Dimethylsila)tetradecyl-3,3-difluoro-5-[5-(4-(perfluoro-1H,1H-heptyloxy)phenyl)pyrimidin-2-yl]-2,3-dihydrofuro[3,2-b]pyridine

Example 196

2-(9-Dimethylsila)tetradecyl-3,3-difluoro-5-[5-(4-(5-oxanonyloxy)phenyl)pyrimidin-2-yl]-2,3-dihydrofuro[3,2-b]pyridine

Example 197

2-(9-Dimethylsila)tetradecyl-3,3-difluoro-5-[5-(4-(5-oxaundecyl)phenyl)pyrimidin-2-yl]-2,3-dihydrofuro[3,2-b]pyridine

Example 198

2-(9-Dimethylsila)tetradecyl-3,3-difluoro-5-[5-(4-(6-dimethyisila)decyloxyphenyl)pyrimidin-2-yl]-2,3-dihydrofuro[3,2-b]pyridine

Example 199

2-(9-Dimethylsila)tetradecyl-3,3-difluoro-5-[5-(4-(9-dimethylsila)tetradecylphenyl)pyrimidin-2-yl]-2,3-dihydrofuro[3,2-b]pyridine

Example 200

2-(9-Dimethylsila)tetradecyl-3,3-difluoro-5-[5-(4-(pentylcarbonyloxy)phenyl)pyrimidin-2-yl]-2,3-dihydrofuro[3,2-b]pyridine

Example 201

4-(5-Octylpyrimidin-2-yl)phenylbenzo[1,3]dioxole-5-carboxylate 5 mmol of benzo[1,3]dioxole-5-carboxylic acid and 4.8 mmol of 4-(5-octylpyrimidin-2-yl)phenol are dissolved in 50 ml of $CH_2Cl_2$, and 5 mmol of DCC and 0.05 mmol of DMAP are added. The mixture is stirred for 18 hours with exclusion of light, the solvent is stripped off vacuo, and the product is purified by column chromatography on silica gel, giving 4-(5-octylpyrimidin-2-yl)phenyl benzo[1,3]dioxole-5-carboxylate.

Phase sequence:

X 94(81) N 126 I

Example 202

4-(5-Octylpyrimidin-2-yl)phenyl 3-benzo[1,3]dioxol-5-yl acrylate

Analogously to Example 201 from 3-benzo[1,3]dioxol-5-yl acrylic acid and 4-(5-octylpyrimidin-2-yl)phenol.

Phase sequence:

X 127(113) N 173 I

2-Substituted benzo[1,3]dioxole-5-carboxylic acids and 2-substituted indane-5-carboxylic acids can be reacted analogously to this example with substituted phenols, pyrimidinols, pyridinols, pyrazinols, pyridazinols, phenyl hydroxybenzoates, phenylpyrimidinols, phenylpyridazinols, phenylpyrazinols, phenylpyridinols, pyridylpyrimidinols, pyridylpyridazinols, pyridylpyrazinols, pyrimidinylpyrimidinols, pyrimidinylpyrazinols, pyrimidinylpyridazinols and pyridazinylpyrazinols.

Example 204

4-(2-Octylsulfanylpyrimidin-5-yl)phenyl benzo[1,3]dioxole-5-carboxylate

Phase sequence:

X 104(75) $S_A$ 113 I

Example 205

4-(5-Octyloxypyrimidin-2-yl)phenyl benzo[1,3]dioxole-5-carboxylate

Phase sequence:

X 116(98) N 162 I

Example 206

4-(4-Octyloxybenzoyloxy)phenyl benzo[1,3]dioxole-5-carboxylate

Phase sequence:

$X_2$ 72(84) X 110 N 177 I

Example 207

4-Octyloxyphenyl benzo[1,3]dioxole-5-carboxylate

Phase sequence:

X 65 I

Example 208

5-Octyloxy-2-[4-(2-octylbenzo[1,3]dioxol-5-ylmethoxy)-phenyl]pyrimidine

By Mitsunobu etherification of 4-(5-octyloxypyrimidin-2-yl)phenol using (2-octylbenzo[1,3]dioxol-5-yl)methanol.

2-Substituted benzo[1,3]dioxol-5-ylmethanols and 2-substituted indane-5-carboxylic acids can be reacted analogously to this example with substituted phenols, pyrimidinols, pyridinols, pyrazinols, pyridazinols, phenyl hydroxybenzoates, phenylpyrimidinols, phenylpyridazinols, phenylpyrazinols, phenylpyridinols, pyridylpyrimidinols, pyridylpyridazinols, pyridylpyrazinols, pyrimidinylpyrimidinols, pyrimidinylpyrazinols, pyrimidinylpyridazinols and pyridazinylpyrazinols.

Example 209

(Benzo[1,3]dioxol-5-yl)-2-(4-octyloxyphenyl)pyridine

Analogously to Example 1 from benzo[1,3]dioxole-5-boronic acid and 4-(5-bromopyrimidin-2-yl)phenyl octyl ether.

Phase sequence:

X 135 N 171 I

Substituted benzo[1,3]dioxole-5-boronic acid derivatives and substituted indane-5-boronic acids can be reacted analogously to this example with substituted bromobenzenes, bromopyrimidines, bromopyridines, bromopyrazines, bromopyridazines, bromophenylbenzoates, bromophenylpyrimidines, bromophenylpyridazines, bromophenylpyrazines, bromophenylpyridines, bromopyridylpyrimidines, bromopyridylpyridazines, bromopyridylpyrazines, bromopyrimidinylpyrimidines, bromopyrimidinylpyrazines, bromopyrimidinylpyridazines and bromopyridazinylpyrazines.

Example 210

5-{5-[2-(4-Hexylphenyl)ethyl]-1,3-dioxan-2-yl}benzo[1,3]dioxole

By reaction of benzo[1,3]dioxole-5-carbaldehyde with 2-[2-(4-hexylphenyl)ethyl]propane-1,3-diol with acid catalysis on a water separator.

Phase sequence:

X 89 I

Substituted benzo[1,3]dioxole-5-carbaldehydes and substituted indane-5-carbaldehydes can be reacted analogously to this example with 1,3-propanediols substituted by bromobenzenes, pyrimidines, pyridines, pyrazines, pyridazines, phenylbenzoates, phenylpyrimidines, phenylpyridazines, phenylpyrazines, phenylpyridines, pyridylpyrimidines, pyridylpyridazines, pyridylpyrazines, pyrimidinylpyrimidines, pyrimidinylpyrazines, pyrimidinylpyridazines and pyridazinylpyrazines.

Example 211

2-[4-(Benzo[1,3]dioxol-5-ylmethoxy)phenyl]-5-octyloxypyrimidine.

By Mitsunobu etherification of 4-(5-octyloxypyrimidin-2-yl)phenol using benzo[1,3]dioxol-5-ylmethanol analogously to Example 208.

Phase sequence:

X 94 N 113 I

Example 212

5-(Benzo[1,3]dioxol-5-ylmethoxy)-2-(4-octyloxyphenyl)pyrimidine

By Mitsunobu etherification of 2-(4-octyloxyphenyl)pyrimidin-5-ol using benzo[1,3]dioxol-5-ylmethanol analogously to Example 208.

Phase sequence:

X 122 N 118 I

Example 213

2-[4-(Benzo[1,3]dioxol-5-ylmethoxy)phenyl]-5-octylpyrimidine

By Mitsunobu etherification of 4-(5-octylpyrimidin-2-yl)phenol using 5 benzo[1,3]dioxol-5-ylmethanol analogously to Example 208.

Phase sequence:

X 91 N 81 I

Use examples

A mixture M1, comprising

| Percent by weight | |
|---|---|
| 9.02 | 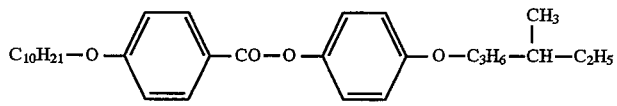 |
| 7.77 | 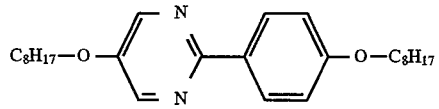 |
| 3.48 | 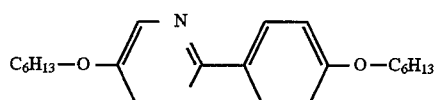 |
| 7.24 | 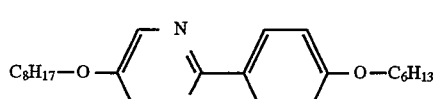 |
| 6.58 | 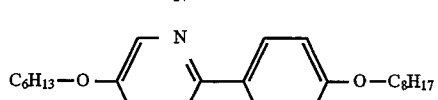 |
| 5.29 | 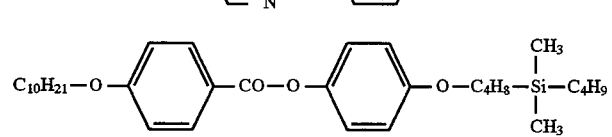 |
| 12.69 | 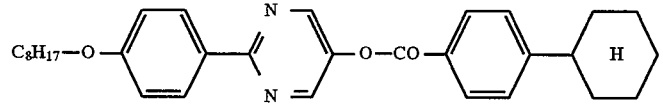 |
| 7.73 | 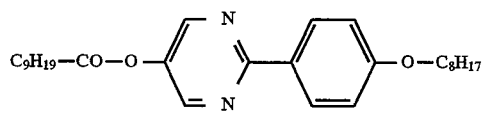 |
| 6.40 | 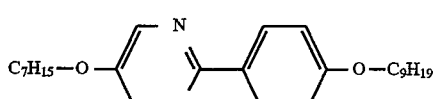 |
| 3.00 | 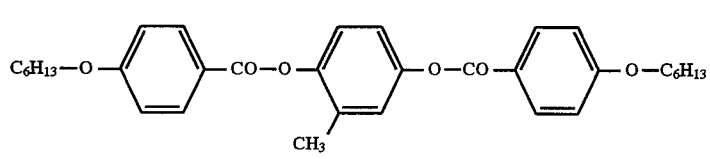 |
| 6.64 | 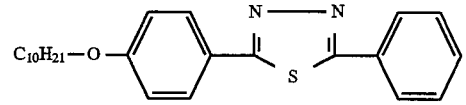 |
| 3.98 | 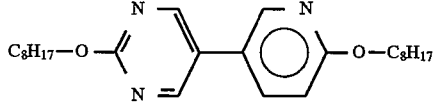 |
| 6.30 | 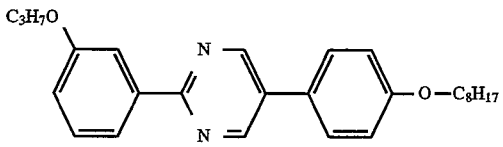 |

| | |
|---|---|
| 5.76 | 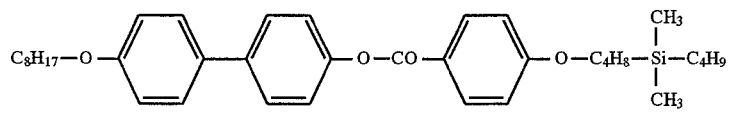 |
| 8.12 | 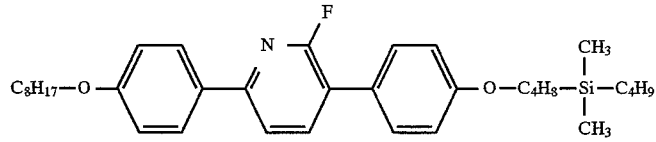 | has the phase sequence:

$S_C$ 79.5° $S_A$ 90.5° N 102 I

In each case 10% by weight, based on the weight of the entire mixture, of a novel substance are added to this mixture (Use Examples 1 to 7), and phase sequences of the resultant mixtures are determined.

Use Example 1

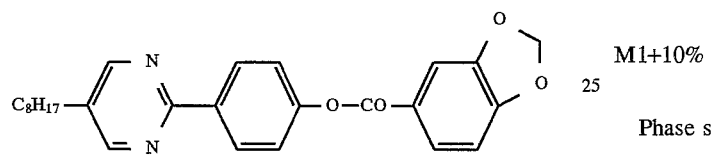

M1+10%
Phase sequence: $S_C$ 73° N 102° I

Use Example 2

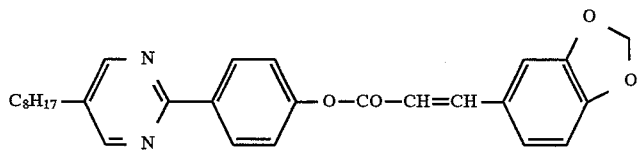

M1+10%
Phase sequence: $S_C$ 72° N 105° I

Use Example 3

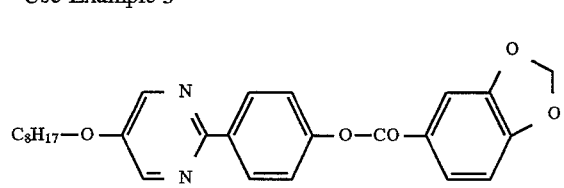

M1+10%
Phase sequence: $S_C$ 75° N 106° I

Use Example 4

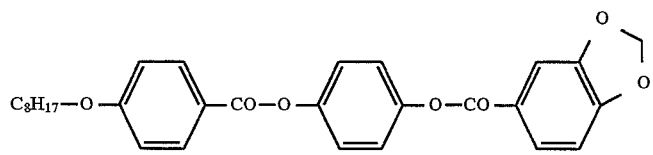

M1+10%
Phase sequence: $S_C$ 75° N 105° I

Use Example 5

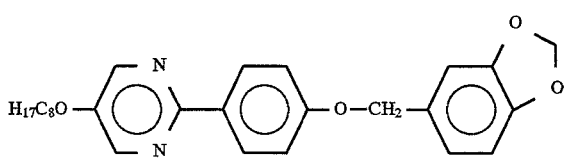

M1+10%

Phase sequence: $S_C$ 79° $S_A$ 94.5° N 108 I

Use Example 6

H₁₇C₈O—[pyridine]—[phenyl]—O—CH₂—[methylenedioxyphenyl]

M1+10%

Phase sequence: $S_C$ 81° $S_A$ 87° N 103° I

Use Example 7

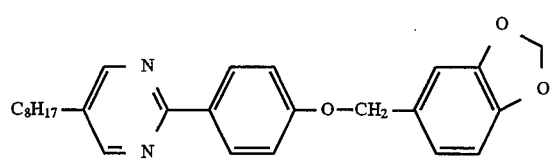

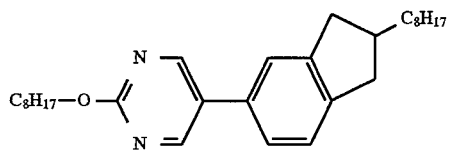

M1+10%

Phase sequence: $S_C$ 76° $S_A$ 83° N 100° I

It can be seen that in all cases the nematic phase is broadened compared with M1.

Use Example 8

A ferroelectric mixture M2 comprises:

are added to the ferroelectric base mixture M2 from Use Example 8. The resultant mixture has a spontaneous polarization $P_S$ of only 49 nC/cm² at 25° C.

The Use Examples confirm that the novel compounds are suitable for the preparation of smectic or ferroelectric liquid-crystal mixtures which have high spontaneous polarization and a nematic phase which is so broad that the alignment of the liquid-crystal mixture is favorably affected on cooling.

| Percent by weight | |
|---|---|
| 79.77 | M1 |
| 3.72 | |
| 3.83 | |
| 4.06 | |
| 7.76 | |
| 0.87 | |

10% by weight, based on the weight of the entire mixture, of the novel compound from Use Example 6 are added to this mixture. The resultant mixture has a spontaneous polarization $P_S$ of 68.5 nC/cm² at 25° C.

Use Example 9

10% by weight, based on the weight of the entire mixture, of the novel compound from Use Example 7 are added to the ferroelectric base mixture M2 from Use Example 8. The resultant mixture has a spontaneous polarization $P_S$ of 66 nC/cm² at 25° C.

Comparative Example

10% by weight, based on the weight of the entire mixture of the prior-art compound

We claim:

1. A ferroelectric liquid crystal mixture, comprising one or more aromatic compounds of the formula (I)

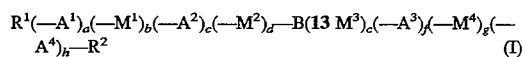

in which the symbols and indices have the following meanings:

B is

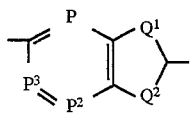

$R^1$ and $R^2$ are identical or different and are hydrogen, or a straight-chain or branched alkyl radical having 1 to 20 carbon atoms (with or without an asymmetrical carbon atom), where one or more —CH$_2$— groups may also be replaced by —O—, —S—, —CO—, —CS—, —CH=CH—, —C≡C—, ∧, —Si(CH$_3$)$_2$—, 1,4-phenylene, trans-1,4-cyclohexylene or trans-1,3-cyclopentylene, with the proviso that oxygen atoms and sulfur atoms must not be bonded directly to one another, and/or one or more H atoms of the alkyl radical may be substituted by —F, —Cl, or —OR$^2$, or are alternatively one of the following chiral groups:

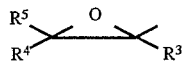

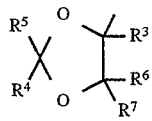

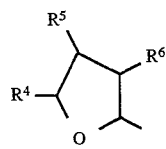

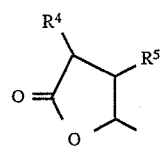

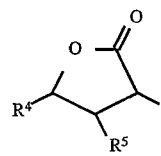

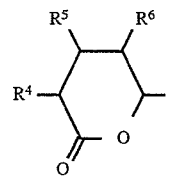

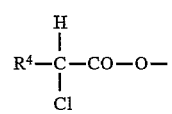

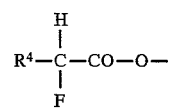

-continued

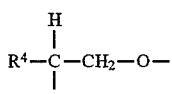

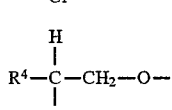

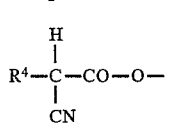

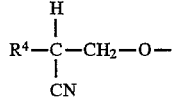

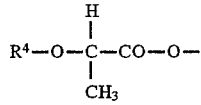

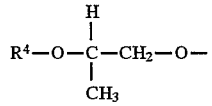

$R^3$, $R^4$, $R^5$, $R^6$ and $R^7$ are identical or different and are hydrogen or a straight-chain or branched alkyl radical having 1–16 carbon atoms (with or without an asymmetrical carbon atom), where one or more —CH$_2$— groups may also be replaced by —O— with the proviso that oxygen atoms must not be bonded directly to one another, and/or one or more H atoms of the alkyl radical may be substituted by —F or —Cl; $R^4$ and $R^5$ may also together be —(CH$_2$)$_4$— or —(CH$_2$)$_5$— if they are bonded to an oxirane, dioxolane, or tetrahydrofuran system;

$Q^1$ and Q2 are identical or different and are CH$_2$, CF$_2$, or O;

$P^1$, $P^2$ and $P^3$ are identical or different and are C—H, C—F or N;

$M^1$, $M^2$, $M^3$ and $M^4$ are identical or different and are —CO—O—, —O—CO—, —CH$_2$—O—, —O—CH$_2$—, —CH=CH—, —C≡C—, —O—CO—CH=CH—, —CH=CH—COO—, —O—CO—CH$_2$—CH$_2$—, —CH$_2$—CH$_2$—COO—, —O—CH$_2$—CH$_2$—CH$_2$—, —CH$_2$—CH$_2$—CH$_2$—O— or a single bond;

$A^1$, $A^2$, $A^3$ and $A^4$ are identical or different and are 1,4-phenylene, in which one or more H atoms may be replaced by F, pyridine-2,5-diyl, in which one or more H atoms may be replaced by F, pyrimidine-2,5-diyl, in which one or two H atoms may be replaced by F, trans-1,4-cyclohexylene, in which one or two H atoms may be replaced by CN and/or CH$_3$, 1,3,4-thiadiazole-2,5-diyl, 1,3-dioxane-2,5-diyl, 1,3-thiazole-2,4-diyl, in which one H atom may be replaced by F, 1,3-thiazole-2,5-diyl, in which one H atom may be replaced by F, thiophene-2,4-diyl, in which one H atom may be replaced by F, thiophene-2,5-diyl, in which one or two H atoms may be replaced by F, naphthalene-2,6-diyl, in which one or more H atoms may be replaced by F;

a, b, c, d, e, f, g and h are zero or one; with the following proviso: if the group B is

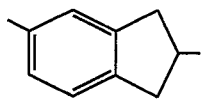

at least one of the radicals R¹ must comprise an —Si(CH₃)₂— and/or

group and/or be one of the following chiral groups:

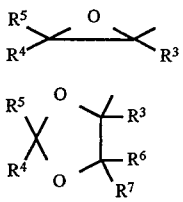

2. A ferroelectric liquid-crystal mixture as claimed in claim 1, wherein the symbols and indices in the formula (I) have the following meanings:

R¹ and R² are identical or different and are hydrogen or a straight-chain or branched alkyl radical having 1 to 18 carbon atoms (with or without an asymmetrical carbon atom), where one or more —CH₂— groups may also be replaced by —O—, —CO—, —CH=CH—, —C≡C—,

,

—Si(CH₃)₂— or trans-1,4-cyclohexylene, with the proviso that oxygen atoms must not be bonded directly to one another, and/or one or more H atoms of the alkyl radical may be substituted by —F, or —O³, or are alternatively one of the following chiral groups:

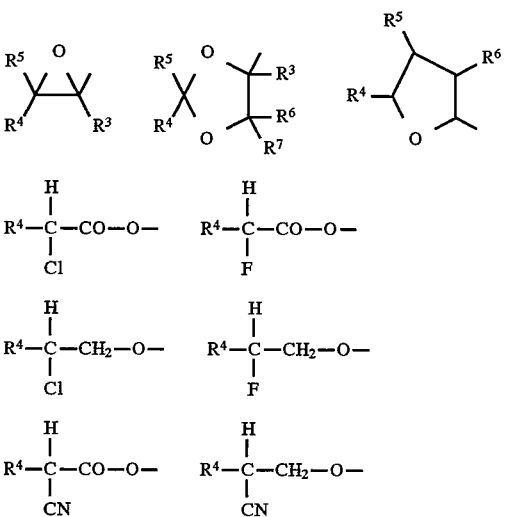

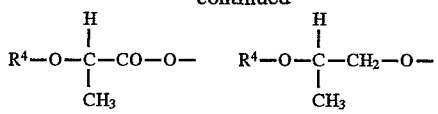

R³, R⁴, R⁵, R⁶ and R⁷ are identical or different and are hydrogen or a straight-chain or branched alkyl radical having 1–16 carbon atoms (with or without an asymmetrical carbon atom), where one or more —CH₂— groups may also be replaced by —O—, with the proviso that oxygen atoms must not be bonded directly to one another, and/or one or more H atoms of the alkyl radical may be substituted by —F or —Cl; R⁴ and R⁵ may also together be —(CH₂)₄— or —(CH₂)₅— if they are bonded to an oxirane, dioxolane, or tetrahydrofuran, system;

Q¹ and Q² are identical or different and are CH₂, CF₂;

P¹, P² and P³ are identical or different and are C—H, C—F or N;

M¹, M², M³ and M⁴ are identical or different and are —CO—O—, —O—CO—, —CH₂—O, —O—CH₂—, or a single bond;

A¹, A², A³ and A⁴ are identical or different and are 1,4-phenylene, in which one or more H atoms may be replaced by F, pyridine-2,5-diyl, in which one or more H atoms may be replaced by F, pyrimidine-2,5-diyl, in which one or two H atoms may be replaced by F, trans-1,4-cyclohexylene, in which one or two H atoms may be replaced by CN and/or CH₃, 1,3,4-thiadiazole-2,5-diyl, or naphthalene-2,6-diyl, in which one or more H atoms may be replaced by F;

a, b, c, d, e, f, g and h are zero or one;

where the proviso in claim 1 applies.

3. A ferroelectric liquid crystal mixture as claimed in claim 1, wherein the symbols and indices in the formula (I) have the following meanings:

B is

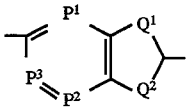

R¹ and R² are identical or different and are hydrogen, or a straight-chain or branched alkyl radical having 1 to 16 carbon atoms (with or without an asymmetrical carbon atom), where one, two or three —CH₂— groups may also be replaced by —O—, —CO—,

, or —Si(CH₃)₂— with the proviso that oxygen atoms must not be bonded directly to one another, and/or one or more H atoms of the alkyl radical may be substituted by —F, or are alternatively one of the following chiral groups:

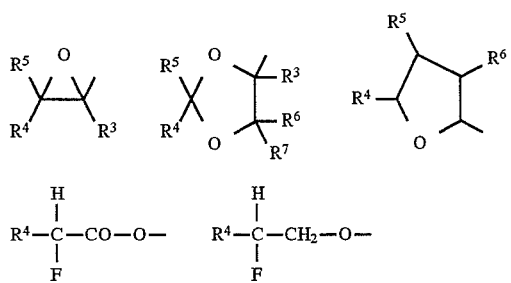

$R^4$—CH(H)(F)—CO—O—  $R^4$—CH(H)(F)—CH$_2$—O—

$R^3$, $R^4$, $R^5$, and $R^6$ are identical or different and are hydrogen or a straight-chain or branched alkyl radical having 1–14 carbon atoms (with or without an asymmetrical carbon atom); $R^4$ and $R^5$ may also together be —(CH$_2$)$_4$— or —(CH$_2$)$_5$— if they are bonded to an oxirane or dioxolane system;

$Q^1$ and $Q^2$ are identical or different and are CH$_2$, CF$_2$, or O;

$P^1$, $P^2$ and $P^3$ are identical or different and are C—H, C—F or N;

$M^1$, $M^2$, $M^3$ and $M^4$ are identical or different and are —CO—O—, —O—CO—, —CH$_2$—O—, —O—CH$_2$—, or a single bond;

$A^1$, $A^2$, $A^3$ and $A^4$ are identical or different and are 1,4-phenylene, in which one, or two H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by CN and/or CH$_3$, or 1,3,4-thiadiazole-2,5-diyl;

a, b, c, d, e, f, g and h are zero or one;

with the proviso that at least one of the radicals $Q^1$, $Q^2$ is —CF$_2$—, —NR$^3$—, —S—, —O— or —CO— and/or at least one of the radicals $P^1$, $P^2$ and $P^3$ is =CF— or =N—.

4. A liquid-crystal mixture as claimed in claim 1, which consists of 2 to 35 individual compounds.

5. A liquid-crystal mixture as claimed in claim 1, which comprises 1 to 10 compounds of the formula I.

6. A liquid-crystal mixture as claimed in claim 1, which comprises from 0.01 to 80% by weight of at least one compound of the formula I.

7. An electro-optical switching and display element comprising a liquid-crystal mixture as claimed in claim 1.

* * * * *